(12) United States Patent
Scott

(10) Patent No.: US 7,010,979 B2
(45) Date of Patent: Mar. 14, 2006

(54) METHOD AND APPARATUS FOR ULTRASONIC SIZING OF PARTICLES IN SUSPENSIONS

(75) Inventor: David Mark Scott, Wilmington, DE (US)

(73) Assignee: E.I. du Pont de Nemours and Company, Wilmington, DE (US)

( * ) Notice: Subject to any disclaimer, the term of this patent is extended or adjusted under 35 U.S.C. 154(b) by 76 days.

(21) Appl. No.: 10/433,868

(22) PCT Filed: Dec. 18, 2001

(86) PCT No.: PCT/US01/49181
§ 371 (c)(1),
(2), (4) Date: Jun. 4, 2003

(87) PCT Pub. No.: WO02/50511
PCT Pub. Date: Jun. 27, 2002

(65) Prior Publication Data
US 2004/0060356 A1 Apr. 1, 2004

Related U.S. Application Data

(60) Provisional application No. 60/256,258, filed on Dec. 18, 2000.

(51) Int. Cl.
*G01N 9/04* (2006.01)

(52) U.S. Cl. ............................. 73/596; 73/602; 73/628; 73/866.5

(58) Field of Classification Search .................. 73/596, 73/61.75, 24.02, 24.03, 61.42, 61.41, 865.5, 73/602, 628, 599
See application file for complete search history.

(56) References Cited

U.S. PATENT DOCUMENTS

| | | |
|---|---|---|
| 3,779,070 A | 12/1973 | Cushman et al. |
| 3,802,271 A | 4/1974 | Bertelson |
| 4,706,509 A | 11/1987 | Riebel |
| 5,121,629 A | 6/1992 | Alba |

(Continued)

FOREIGN PATENT DOCUMENTS

EP 0989397 3/2002

OTHER PUBLICATIONS

PCT/US01/49181 International Search Report dated Apr. 17, 2003.
Patricia Mougin, Derek Wilkinson, Kevin Roberts and Richard Tweedle, Characterizations of particle size and its distribution during the crystallization of organic fine chemical products as measured in situ using ultrasonic attenuation spectroscopy, J. Acoust. Soc. Am., 109 (1) 274–282, Jan. 2001.

(Continued)

*Primary Examiner*—Hezron Williams
*Assistant Examiner*—Jacques M Saint-Surin

(57) ABSTRACT

A particle size distribution monitor, comprising: a transducer adapted to be a source of ultrasonic energy and positioned in contact with a suspension containing a percent by volume of particles in a liquid, the transducer transmitting ultrasonic energy through the suspension wherein the energy comprises a wideband pulse containing a range of frequency components; a transducer adapted to be a receiver of ultrasonic energy and positioned in contact with said suspension to receive said wideband range of ultrasonic energy which has passed through the suspension; a first means adapted to accept a signal from said receiver and make an instantaneous determination of the attenuation of the wideband ultrasonic energy in passing through the suspension. A method of monitoring the particle size distribution of particles in a suspension under dynamic conditions, comprising the steps of: transmitting a first pulse of ultrasonic energy containing a wideband range of frequency components through the suspension which attenuates the pulse; receiving the attenuated pulse after it has passed through the suspension; developing a first signal representative of the attenuated first pulse; digitizing the first signal with a high speed analog-to-digital converter to form a time domain signal; applying a Fourier transform to convert the time domain signal to an equivalent frequency domain signal, or spectrum, for each signal; converting the spectrum into dB to express the attenuation as a function of frequency.

6 Claims, 15 Drawing Sheets

U.S. PATENT DOCUMENTS

| | | | |
|---|---|---|---|
| 5,389,122 A | | 2/1995 | Glicksman |
| 5,483,226 A | * | 1/1996 | Menut .......................... 340/621 |
| 5,569,844 A | | 10/1996 | Sowerby |
| 5,831,150 A | | 11/1998 | Sowerby et al. |
| 5,969,237 A | | 10/1999 | Jones et al. |
| 6,109,098 A | | 8/2000 | Dukhin et al. |
| 6,119,510 A | * | 9/2000 | Carasso et al. ............ 73/61.75 |
| 6,487,894 B1 | * | 12/2002 | Dukhin et al. ............. 73/61.75 |
| 6,604,408 B1 | * | 8/2003 | Dosramos et al. ......... 73/61.75 |
| 6,748,815 B1 | * | 6/2004 | Povey et al. ............... 73/865.5 |

OTHER PUBLICATIONS

Hemant P. Pendse and Arvind Sharma, Particle Size Distribution Analysis of Industrial Colloidal Slurries Using Ultrasonic Spectroscopy, Part. Part. Syst. Charact., 10 (1993) 229–233.

A. K. Holmes and R. E. Challis, Ultrasonic scattering in concentrated colloidal suspensions, Colloids and Surfaces A: Physicochemical and Engineering Aspects, 77 (1993) 65–74.

J. R. Allegra and S. A. Hawley, Attenuation of Sound in Suspensions and Emulsions: Theory and Experiments, J. Acoust. Am., 51 (1972) 1545–1584.

Andrew K. Holmes, Richard E. Challis and David J. Wedlock, A Wide Bandwisth Study of Ultrasound Velocity and Attenuation in Suspensions: Comparison of Theory with Experimental Measurements, J. Colloil Interface Sci., 156 (1993) 261–268.

P.C. Waterman and Rohn Truell, Multiple Scattering of Waves, Journal of Mathematical Physics, 2 (1981) 512–540.

P. Lloyd and M. V. Berry, Wave propaganda through an assembly of sphered IV. Relations between different multiple scattering theories, Proc. Phys. Soc., 1967, vol. 91 678–688.

Ulrich Riebel and Friedrich Loffler, The Fundamentals of Particle Size Analysis by Means of Ultrsonic Spectrometry, Part. PArt. Syst. Charac., 6 (1989) 1335–143.

* cited by examiner

US 7,010,979 B2

METHOD AND APPARATUS FOR ULTRASONIC SIZING OF PARTICLES IN SUSPENSIONS

CROSS REFERENCE TO RELATED APPLICATIONS

This application claims the benefit of U.S. Provisional Application No. 60/256,258, filed on Dec. 18, 2000.

BACKGROUND OF THE INVENTION

This invention pertains to the field of particle size measurement of industrial particles and more specifically to the on-line measurement of the particle size distribution (PSD) of particles in a liquid suspension. By suspension is meant a solid or liquid discrete particle in a liquid carrier or matrix. Examples of suspensions of interest are a slurry (a high concentration of more than about 10% to 15% solid particles by volume in a liquid), a dispersion (a low concentration of less than about 10% to 15% solid particles by volume in a liquid), and an emulsion (liquid particles or droplets in a liquid). It relates to the measurement of PSD of sub-micron sized particles in a suspension, and in systems with particle sizes larger than 1 micron. It also relates to systems used to determine the concentration and the degree of agglomeration in multiphase systems. It relates to systems useful in various industrial applications including emulsification (droplet size), homogenization (quality of dispersion), grinding (particle size distribution), precipitation of metals (particle agglomeration), and on-line measurement of particle formation (particle size distribution).

It is known that the frequency-dependent attenuation of ultrasound in suspensions is determined by the PSD within those systems (the "Forward Problem"). Several theoretical models have been developed to treat the absorption of the ultrasound for a variety of systems. In particular, Allegra and Hawley [Attenuation of Sound in Suspensions and Emulsions: Theory and Experiments. *J. Acoust. Soc. Am.* 51 (1972) 1545–1564] provide a mathematical framework for calculating the attenuation of ultrasound in dispersions and emulsions. The Allegra-Hawley model is completely general, allowing one to calculate the absorption for new systems without having to develop new models. Although this theory is for monodisperse (single-sized) suspensions at low volume concentrations (20% or less), it is easily extended to polydisperse systems by integrating the calculated absorption over the PSD density function.

Holmes and Challis [Ultrasonic Scattering in Concentrated Colloidal Suspensions. A. K. Holmes, R. E. Challis in *Colloids and Surfaces A: Physicochemical and Engineering Aspects* 77 (1993) 65–74; and A Wide Bandwidth Study of Ultrasound Velocity and Attenuation in Suspensions: Comparison of Theory with Experimental Measurements. A. K. Holmes, R. E. Challis, D. J. Wedlock in *J. Colloid Interface Sci.* 156 (1993) 261–268] have measured absorption and phase velocity in monodisperse polystyrene suspensions of up to 45% volume fraction and found good agreement with the predictions of single and multiple scattering models [Multiple Scattering of Waves. P. C. Waterman, R. Truell in *J. Math. Phys.* 2 (1961) 512–540, and Wave Propagation Through an Assembly of Spheres IV: Relations Between Different Multiple Scattering Theories. P. Lloyd, M. V. Berry in *Proc. Phys. Soc.* 91 (1967) 678–688]. Holmes and Challis use a wide-band pulse combined with a high-speed digitizer and a Fourier Transform operation to acquire the ultrasonic spectrum. They use a pair of transducers at a fixed separation for an off-line, through-transmission measurement, and ignore all but the primary transmitted pulse. They do not demonstrate the ability to measure PSD with their apparatus.

Since a known PSD can be used to predict the absorption as a function of frequency, it should also be possible to invert ultrasonic spectra to predict the PSD based only on the absorption ("the Inverse Problem"). It turns out that inverting the ultrasonic data is an art in itself, as variations in this data cause instability in the standard inversion methods.

Much of the ultrasonic work to date has been concerned with measuring the size of relatively coarse particles (>10 microns). One of the first ultrasonic-based instruments was the Armco Autometrics® PSM-400 [Particle Size and Percent Solids Monitor. C. Cushman, J. Hale, V. Anderson in U.S. Pat. No. 3,779,070 (1973)], used to control grinding circuits in the mineral industry. It used narrowband, stationary transducer pairs (each pair operating at a single fixed frequency) and a semi-empirical model to provide an indication of median particle size (max. 600 micron).

U.S. Pat. No. 3,779,070 to Cushman et al in FIGS. 37 to 39 shows an arrangement of separate sending and receiving ultrasonic transducers on opposite sides of a ore slurry flow passage or transducers (which both send and receive) on one side and an ultrasound reflector on the opposite side. The transducers are in direct contact with the slurry. Slurries with mean particle diameters of from 40 to 250 microns are discussed. Separation of the transducers is about 4.0 inches (10.2 cm). The flow passage is placed directly in a container (sump) of slurry or a slurry pipeline. One or two pairs of transducers may be used. When two transducer pairs are used, each operates alternately, one to determine particle size and the other to determine percent solids in essentially the same volume of the slurry. Two different ultrasonic frequencies may be used depending on the attenuation expected from the sample, but once a frequency is selected it remains constant. Selected frequencies may be within the range of about 0.3 to 3.0 MHz for particle size distributions with a median size of about 150 microns or smaller. In cases where a single pair of transducers are used (in a system using a reflector), the two transducers operate alternately at two different frequencies. The ultrasonic particle size measuring system provides real-time results and may be part of a feedback loop for automatic control of a circuit for ore grinding. Two major limitations are that any variations in the concentrations must be known and the size distribution is not measured with this method.

Riebel and Loffler [The Fundamentals of Particle Size Analysis by Ultrasonic Spectrometry. *Part. Part. Syst. Charact.* 6 (1989) 135–143] obtain an acoustic attenuation spectrum (2–80 MHz) with one pair of wideband transducers to infer the entire PSD for particles ranging between 20 and 1000 microns. Their physical model is based on the Lambert-Beer law (max. concentration 10% vol) and the assumption that the particle size-dependent attenuation at each applied frequency is proportional to the total particle surface encountered by the sound wave traversing the medium. This assumption is valid only in the short wavelength limit.

U.S. Pat. No. 4,706,509 (1987) to Riebel discloses using ultrasound for sampling multiple particle size intervals to determine a particle size distribution preferably with 5 or more particle size intervals. A number of different discrete ultrasonic frequencies are successively passed as tone bursts through a suspension of particles in a liquid; preferably the number of frequencies equals the number of intervals sampled. One or more pairs of ultrasonic transmitters and receivers may be used for through transmission measurements, or the same transducers can serve as both a transmitter and receiver of the echo resulting from an opposed reflector. If a plurality of ultrasonic wave transmitters are excited continuously standing waves are avoided by arranging the absorption path at an angle other than 90 degrees to the walls of the suspension enclosure. Preferably, the frequencies selected for excitation are such that the wavelength corresponding to the lowest frequency is greater than the diameter of the largest particles to be expected, and the wavelength corresponding to the highest frequency is less than the diameter of the smallest particles to be expected. The frequency range contemplated by Riebel would therefore limit his method to particles larger than 15 microns. Extensive calibration of the system is required, and changes in particle morphology have been observed to require a new calibration.

Recent work has tried to extend ultrasonic-based measurements to cover the sub-micron particle size regime. Pendse and Sharma [Particle Size Distribution Analysis of Industrial Colloidal Slurries Using Ultrasonic Spectroscopy. *Part. Part. Syst. Charact.* 10 (1993) 229–233] report on a prototype instrument named the AcoustoPhor® (Pen Kem 8000) which comes in both off-line and on-line versions. With this system the acoustic attenuation is measured at several discrete frequencies between 1 and 100 MHz. At these frequencies viscous energy dissipation of the sound wave is the dominant phenomenon for sub-micron, rigid particles. These authors Claim to be able to determine the PSD in the range of 0.01 to 100 microns for slurry concentrations as high as 50% (vol).

U.S. Pat. No. 5,121,629 (1992) to Alba uses the more general Allegra-Hawley model (which includes viscous, thermal, and scattering components) as the basis for an off-line instrument (Malvern UltraSizer) that measures PSD in the range of 0.01 to 100 microns for slurries with concentrations up to 50% (vol). In this patent, Alba uses two wideband ultrasonic transmitters and receivers working at selected, discrete frequencies within the 0.5 to 100 MHz range to determine particle size distribution and concentration for sizes smaller than a micron and concentrations higher than 15% by volume. He suggests that different embodiments could use arrangements like pulse-echo, tone burst transmission/detection, or multiple transducers. Off-line calculated attenuation spectra are compared to on-line measured attenuation spectra of the test sample to rapidly estimate the size distribution and concentration via a fitting routine. He suggests the method is applicable to both off-line and on-line operation, but it has been observed that the preferred embodiment of the instrument requires 4–5 minutes to collect and process the data for the discrete frequencies as taught. This system is inappropriate for in-line measurements on rapidly flowing suspensions or suspensions undergoing rapid changes.

U.S. Pat. No. 3,802,271 to Bertelson uses an acoustic signal to analyze particles in a fluid, preferably combustion dust particles in industrial smokestack emissions. He avoids the need to scan frequencies by employing a complex wave shape of a non-sinusoidal waveform comprehending several frequency components. Contemplated are rectangular, square, or sawtooth waveforms that are generated by a variable frequency oscillator that drives a speaker directly or through a pulse generator. The apparatus is said to be useful by using either a frequency scan or a single non-sinusoidal waveform. The method for analyzing particles includes the step of generating sound wave energy having plural frequency components and transmitting it through the fluid with and without the particles. A major limitation is his requirement of a physical means to separate particles from the fluid so as to provide an acoustic path without particles.

U.S. Pat. No. 5,831,150 to Sowerby et al uses a plurality of ultrasonic beams with discrete frequencies to measure particle sizes in the sub-micron range, such as $TiO_2$ particles in paint samples. Solid content, however, was at a low percentage, such as 2.3%. One embodiment of the invention uses six pairs of piezoelectric transducers to transmit and receive ultrasound of specific frequency. Alternatively, fewer wideband ultrasonic transducers can be used to generate the tone bursts. In all of the disclosed embodiments, the PSD is estimated from the ultrasonic phase velocity. A limitation is the use of a radioactive density gauge to measure the concentration, which is used as an input to the ultrasonic sensor.

The above instruments, in their preferred embodiments, are similar in that they measure the attenuation spectrum one frequency at a time, using either swept-frequency ("chirp") generators or a series of tone-bursts. That approach works well in the laboratory, but it is comparatively slow at collecting data. For on-line application, the sample in the flow cell is changing as the data is collected; consequently, the upper and lower frequency components measured at different times do not relate to the same moving physical particles. Other instruments that use so-called "pulse" generators actually produce a pulse train, which is equivalent to a tone burst (essentially a single frequency or a narrow band of frequencies); such instruments must generate successive tone bursts at several frequencies to measure the attenuation spectrum.

The choice of frequencies in the 1–100 MHz range taught by the prior art imposes a severe restriction on the maximum separation between the transducers: for a suspension having a high concentration of sub-micron particles (10%–50%), the attenuation is so high in that range that the maximum gap can be only a fraction of an inch (typically 0.05–0.10 inch, 0.13–0.26 cm). Small transducer gaps are not well suited for on-line applications, since such small clearances tend to become plugged. Milling operations such as media mills and attritors are designed to reduce the particle size in solid/liquid slurries. The slurries tend to be concentrated (ranging from 20–50% solids by volume), and in the case of sub-micron particles there are no in-line commercial instruments that can measure either particle size or particle size distribution (PSD) of undiluted suspension without becoming plugged after brief operation.

In order to invert spectral data into PSD, most of the prior art (except Alba and Sowerby) uses a phenomenological model as opposed to a physical model. Therefore the task of switching a particular instrument from one process stream to another requires new calibration curves to be developed.

There is a need for a method for obtaining particle size distribution and concentration that allows faster data acquisition at a lower system cost than previous instruments. There is a need for a system that can operate in an industrial environment and obtain on-line results with robust, reliable performance that requires minimal maintenance and avoids a narrow transducer gap prone to plugging. There is a need for a system to invert ultrasonic spectral data into PSD based on a physical model where switching the instrument from one process stream to another requires only substituting the appropriate physical constants.

In the production of precipitated particles for certain applications, there is a need to monitor variations in an aging master batch of solution so that sub-batches can be withdrawn at appropriate times to produce particles of the correct size when combined with a reducing solution that causes precipitation. U.S. Pat. No. 5,389,122 to Glicksman teaches a system for preparing finely divided, spherical shaped silver particles (typically 1–3 microns) using a chemical aging and precipitation process. In the master, the particle size is changing during the aging process, and any sample pulled would still be so reactive that an accurate particle size could not be obtained. There is a need for a PSD system using a simple probe that can rapidly and accurately predict particle size and interact with an automated control system to regulate the addition of a material (such as a reducing agent) to form a finely divided, spherical particle size in a stirred tank system.

SUMMARY OF THE INVENTION

A particle size distribution monitor, comprising: a transducer adapted to be a source of ultrasonic energy and positioned in contact with a suspension containing a percent by volume of particles in a liquid, the transducer transmitting ultrasonic energy through the suspension wherein the energy comprises a wideband pulse containing a range of frequency components; a transducer adapted to be a receiver of ultrasonic energy and positioned in contact with said suspension to receive said wideband range of ultrasonic energy which has passed through the suspension; a first means adapted to accept a signal from said receiver and make an instantaneous determination of the attenuation of the wideband ultrasonic energy in passing through the suspension.

A method of monitoring the particle size distribution of particles in a suspension under dynamic conditions, comprising the steps of: transmitting a first pulse of ultrasonic energy containing a wideband range of frequency components through the suspension which attenuates the pulse; receiving the attenuated pulse after it has passed through the suspension; developing a first signal representative of the attenuated first pulse; digitizing the first signal with a high speed analog-to-digital converter to form a time domain signal; applying a Fourier transform to convert the time domain signal to an equivalent frequency domain signal, or spectrum, for each signal; converting the spectrum into dB to express the attenuation as a function of frequency.

The invention is an ultrasonic PSD analyzer that uses a pulsed (time domain) technique rather than the chirp or tone-burst (frequency domain) techniques of the prior art. The invention uses a single short duration, wideband pulse, which contains sufficient bandwidth to obtain the entire required frequency spectrum for the sub-micron material being analyzed. The single wideband pulse containing a wide spectrum of frequencies enables one to acquire the entire spectrum of interest in an instant. A preferred embodiment of the invention includes a limitation on the frequency range to low frequencies that use longer acoustical paths that permit large gaps between transducers in slurries having a high concentration of sub-micron particles.

The apparatus in one embodiment consists of a single wide-band ultrasonic transducer mounted in a flow cell, an ultrasound reflector, a pulse generator, an amplifier, an analog-to-digital converter (A/D), and a computer. A wideband pulse is launched into the suspension via the transducer, and the resulting echo train from a reflector on the far wall of the flow cell passing back through the suspension is analyzed to obtain the frequency-dependent attenuation per unit length of the suspension. Information from multiple echoes are collected. The particle size distribution (PSD) of the suspension can be determined from this ultrasonic spectrum through the application of an appropriate physical model.

In another embodiment, an ultrasonic transducer is positioned opposite a receiver for once-through transmission of the ultrasonic signal. The transmitter and receiver may be mounted on opposite sides of a material passage or container, or may be mounted in a probe attached to one side of the passage or container with the transmitter and receiver placed a fixed distance apart. In both embodiments, the minimum gap in the acoustic pathway through which the suspension flows is at least 0.25 inches (0.64 cm) to minimize the chance of sediment build up and clogging.

The invention is also a control method for a precipitating particle production system. A master batch of solution is monitored using the ultrasonic system of the invention and the attenuation is used to control the withdrawal and precipitation of sub-batches in order to obtain a desired particle size distribution.

DETAILED DESCRIPTION OF THE FIGURES

Figure 1:
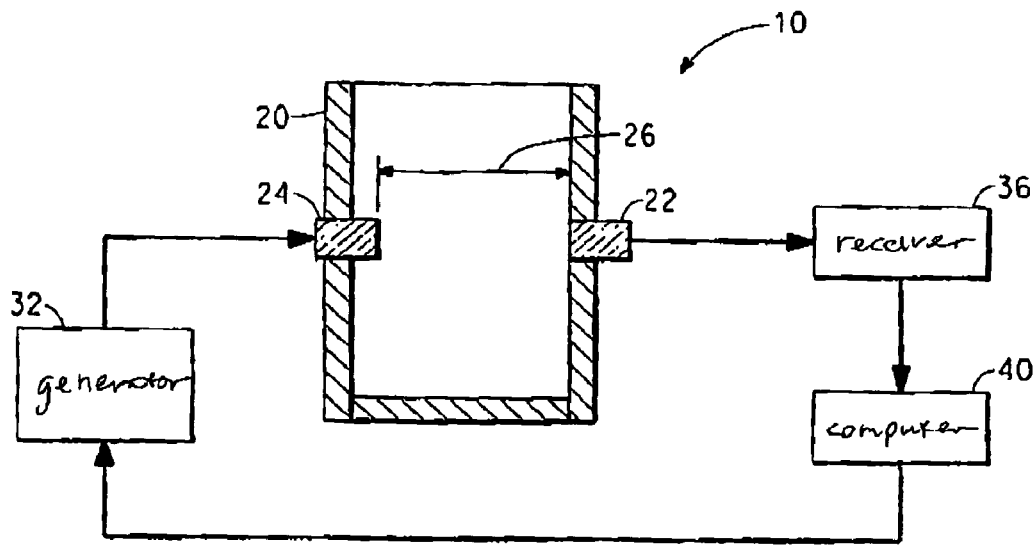
FIG. 1 is a schematic of the prior art using two transducers.

FIG. 1 shows in schematic form a typical instrument 10 common in the prior art. The suspension to be measured is placed in a sample cell 20, which includes an ultrasonic transmitting transducer 24 and an ultrasonic receiving transducer 22. One of these transducers typically may be moved to provide a variable gap 26 between the transducers. A programmable tone-burst generator 32 drives the transmitting transducer 24 in a series of tone bursts at a number of predetermined frequencies. The ultrasonic pulse resulting from each tone burst propagates though the suspension and reaches the receiving transducer 22, where it is converted to an electrical signal. The amplitude of the transmitted signal is measured by a tuned receiver 36. The signal amplitude from the tuned receiver 36 is stored by the computer 40, which initiates the next tone burst in the sequence. At the completion of the tone-burst sequence, the computer 40 has acquired the transmission amplitude as a function of frequency. This data, once converted to dB units, constitutes the transmission spectrum.

It should be noted that the observed transmission signal includes a contribution due to the intrinsic frequency response of the transducer. Also there is an insertion loss at the transducer/suspension interface due to reflection of the ultrasound at the acoustic discontinuity. Therefore the intrinsic instrument response must be subtracted from the measured attenuation in order to measure the attenuation of the suspension. Mechanical loading effects (which depend on the density of the suspension) can change the intrinsic response of the transducer. The correct determination of the intrinsic response obviously impacts the accuracy of the attenuation measurement.

The typical prior art technique shown in FIG. 1 uses a through-transmission method in which the spectrum is measured at two transducer separations to correct for system element variations, or additional transducers may be used. To obtain the attenuation of the suspension, the difference between the "far" separation transmission spectrum (in dB) and the "near" separation transmission spectrum is divided by the change in the acoustic path length between the near and far separations. This technique accounts for transducer loading and changes in intrinsic response, but it is slow and requires a movable transducer. When the suspensions comprise high concentrations of particles, at the high frequencies commonly used, the separation or gap where the suspension is flowing between transducers must be reduced to counter the high attenuation if the signal strength remains the same. This presents a problem of gap clogging with the particles.

An improvement to the prior art provides the following important characteristics of the invention:

(1) the use of single wideband pulses (time domain signal acquisition);
(2) the use of a large gap between transducers and the limitation of the frequency range to allow longer acoustical paths therebetween;
(3) the design of the flow cell to improve the ultrasonic signal; and
(4) the use of signal conditioning (such as logarithmic amplification) to improve the dynamic range of the instrument.

Two basic systems of practicing the invention are contemplated for a PSD monitor and method of operation. In a first system, the suspension comprises a high concentration equal to 15% or greater of solid particles (a dense suspension or slurry) that is commonly encountered in a milling process; preferably the concentration is 25% or greater, but in some cases a concentration of 10% or greater may be considered a high concentration for purposes of this invention. A wideband ultrasonic transmitting transducer operating at a relatively low center frequency (5 MHz or less) is mounted on one side of a passage (or flow cell installed in a pipe carrying the suspension), and a wideband ultrasonic receiving transducer is mounted on an opposite side of the passage, or alternatively a single transmitting and receiving transducer is on one side of the passage and a reflector is mounted on the opposite side. The flow cell may be mounted at the exit of the mill for continuous milling applications or in the recirculation pipe for batch milling applications. In situations where the concentration is 15% or more, empirical models may be applied as is taught in the '629 reference to Alba for handling concentrations up to about 70%. For reference, it is noted that for close packed, single sized, spherical particles, the maximum concentration in a volume is about 50%). Preferably, the wideband pulse has a center frequency of from 100 kHz to 5 MHz for determining the attenuation in a suspension comprising particles which make up 10% or more by volume of the suspension.

In a second system where the volume concentration is 15% or less for solid particles (or in the case of many emulsions, at concentrations of up to 50%), an Allegra-Hawley model (or similar approach modified for multiple scattering) may be used to determine the PSD and particle (or droplet) concentration. The suspension may comprise a very low concentration of sub-micron particles (a dispersion below about 1% particles by volume). Two wideband ultrasonic transducers spaced opposite one another for transmitting and receiving at a high center frequency (e.g. 25 MHz or more) are mounted on a probe that can be inserted into a process vessel (such as a stirred tank); the transducers may also be mounted in a flow cell mounted in process piping. The transducers are mounted facing each other so that they are ultrasonically coupled via an acoustic path through the dispersion. Alternatively, a single wideband transducer may be mounted opposite a reflector for transmitting and receiving the ultrasonic pulse. Either the Allegra-Hawley model or an empirical model (such as a calibration ladder created in off-line measurements of a sample) may be used to infer the PSD and concentration, or the attenuation data itself can be correlated directly with a process parameter of interest. Preferably, the wideband pulse has a center frequency of from 5 MHz to 50 MHz for determining the attenuation in a suspension comprising particles which make up 15% or less by volume of the suspension.

In the preferred embodiment of both systems, a wideband ultrasonic pulse is generated and received by the transducers. A digitizer (analog to digital converter) is used to capture the time domain signal. This signal is converted into the frequency domain by a Fourier transformation or one of its algorithmic implementations (such as a fast Fourier transform FFT or digital Fourier transform DFT). The transmitted ultrasonic spectrum is converted into an attenuation spectrum, which is used to determine the PSD and concentration. It is contemplated that foreknowledge of the concentration of the suspension, obtained from densitometer measurements or knowledge of the batch components, would benefit the determination of PSD.

Figure 2:
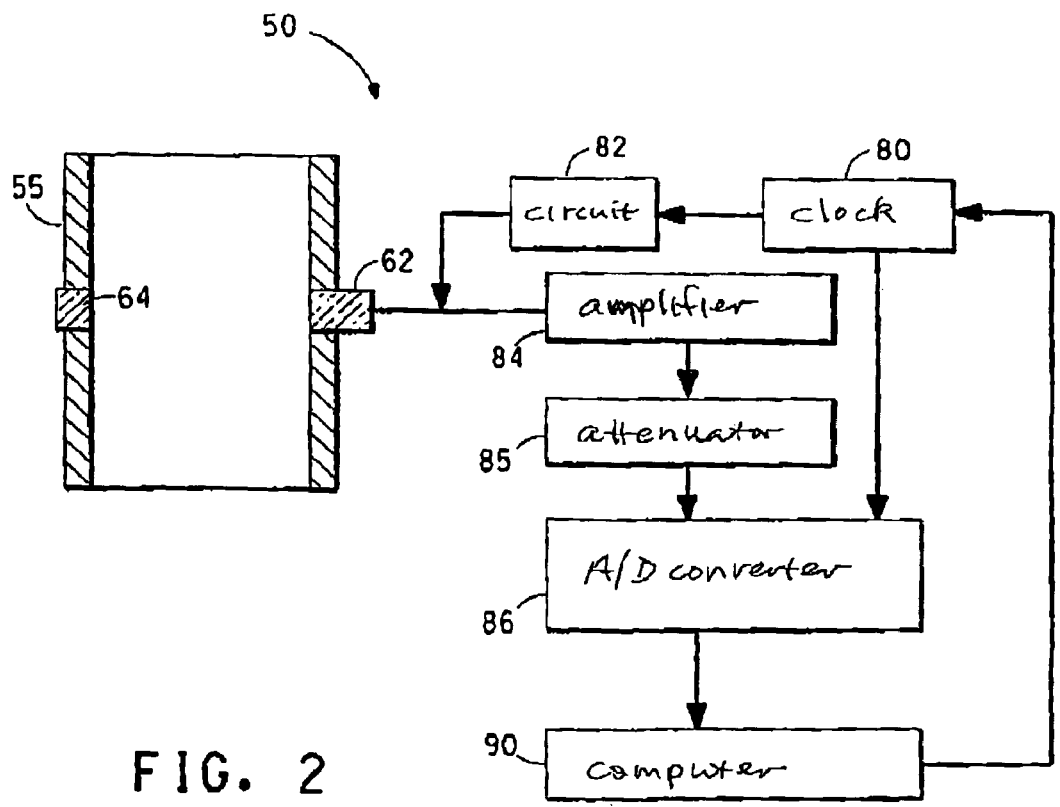
FIG. 2 is a schematic of the preferred embodiment of the invention using one transducer.

One preferred embodiment of the present invention uses a single transducer to launch a wideband ultrasonic pulse into the suspension and to receive the resulting echo train. The term "wideband" means that the pulse contains component frequencies covering a wide range of frequencies (e.g., 200–800 kHz for concentrated suspensions, such as slurries, 15–80 MHz for dilute suspensions of submicron particles such as in a precipitation process). FIG. 2 shows in schematic form a preferred embodiment 50 of the invention. The flow cell 55 is comprised of a pipe section through which flows the suspension to be measured, an ultrasonic transducer 62, and an ultrasound reflector 64. This reflector 64 may be the far wall of the flow cell 55, but in the preferred embodiment it is an ultrasound reflector designed to maximize reflection and minimize reverberations within the reflector itself. The reflector (64) must be designed so that only front-surface reflections are returned; otherwise, back surface reflections will interfere with the ultrasonic signal. For this reason, the opposite side of the pipe generally is not used as a reflector. In the preferred embodiment, the reflector 64 is mounted so that its front surface is flush with the inside surface of the flow cell 55. The system clock 80 is a circuit that provides a trigger signal to the pulser circuit 82 that drives the transmitting transducer 62. The pulser 82 generates a single wideband electrical pulse of short duration. The electrical pulse typically has a duration of 10 Ns and an amplitude between 5–300 volts. The transducer (62) converts this electrical pulse into a wideband ultrasonic energy pulse containing a range of frequency components, which is launched into the suspension flowing through the cell. The ultrasonic pulse propagates though the suspension, bounces off the reflector 64, and returns to the transducer 62, where some of its energy is converted to an electrical signal as the transducer now acts as a receiver. As the ultrasound propagates, it is attenuated according to the concentration, particle size distribution, and composition of the suspension. The rest of the energy continues to propagate as an ultrasonic wave from the surface of the transducer 62 to the reflector 64, returning to the transducer 62 where more of the energy is converted to an electrical signal. Each round trip of the ultrasonic pulse adds another echo to the received signal, so that the total signal is composed of many echoes of the original single pulse. This signal is amplified by a wideband preamplifier 84 with sufficient bandwidth to preserve the spectral content of the echoes. The preamplifier 84 preferably includes a logarithmic amplifier (i.e. an amplifier with a logarithmic transfer function) which compresses the dynamic range of the signal. The amplified signal is further conditioned by a variable attenuator 85 and digitized by a high-speed analog-to-digital (A/D) converter 86, which is triggered by the system clock 80. The digitized signal from the A/D converter 86 is read by the computer 90, which converts the time domain signal into the frequency domain (ultrasonic spectra). The computer 90 may provide the signal used as the system clock 80. The computer also stores information about the intrinsic response of the fluid system (typically the attenuation of the ultrasonic signal in water) and subtracts this from the collected signal to obtain normalized data. The computer also stores characteristic data for different distributions of particle sizes and compares the normalized data to the stored PSD data to determine the best fit to describe the actual particle size distribution.

Ultrasonic propagation parameters (such as sound speed and attenuation) can vary widely in industrial processes, so the instrument must be able to cope with these changes. The computer controls the attenuator 85 to maximize the signal input to the converter 86 without exceeding the voltage range of the A/D converter, thus extending the effective dynamic range of the converter 86. The computer 90 executes a program of instructions that regulates the attenuator 85, controls the digitizer 86, and selects (i.e. "gates") the correct portions of the digitized signal corresponding to the echoes. The gate is typically 10 microseconds or less to exclude reverberations within the transducer itself. Because temperature determines the speed with which the sound propagates through the suspension, even minor changes in suspension temperature will alter the echo timing to the point where it will fall outside the gate. Therefore the computer software tracks the changes in the position of the echo and updates the gate position to keep it centered on the selected pulse echo.

Figure 3A:
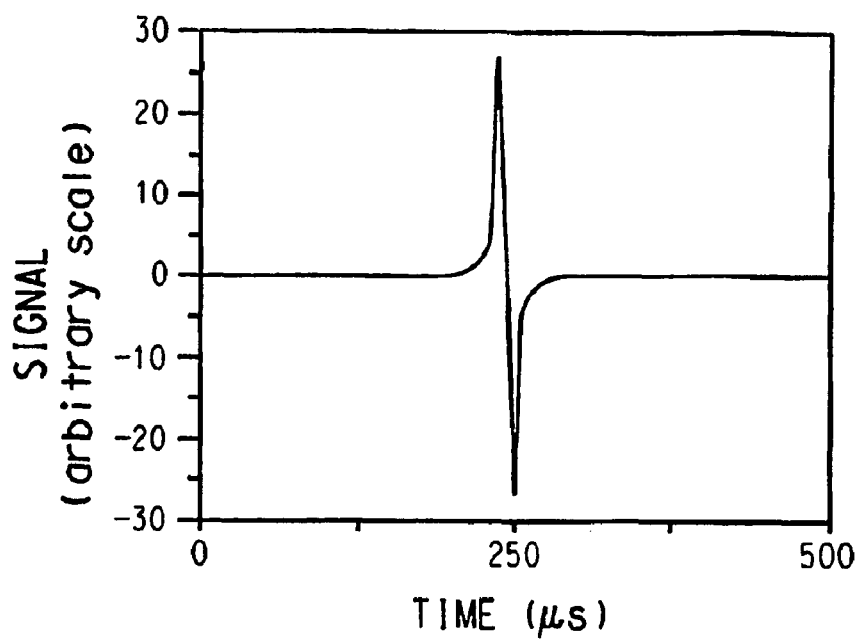
FIGS. 3A and 3B are graphs showing the shape of a typical pulse in the time domain (3A) and in the frequency domain (3B).
Figure 3B:
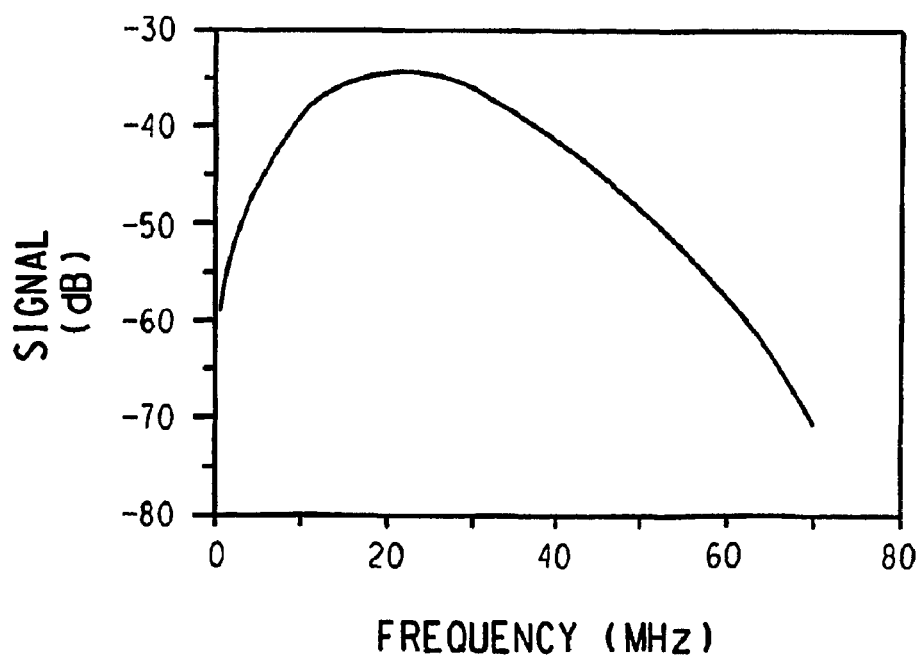

FIG. 3A shows the time-domain pulse generated by the pulser. It is a well-known mathematical result that any time-domain signal can be resolved into its component frequencies via a Fourier transformation. The bandwidth of the resulting spectrum is inversely proportional to the duration of the corresponding time-domain pulse. Thus, the frequency components of this input pulse are shown in FIG. 3B. In FIG. 3B, the frequency has a range of from about 1 MHz to 70 MHz and a center frequency of about 35 MHz in the center of this range. The center frequency may not exactly align with the frequency having the highest signal strength, 25 MHz, but it is usually close to it. In the practice of this invention, it is preferred that the range of the wideband frequency is defined by the center frequency plus and minus about 25% to 70% of the center frequency value; and most preferably about 50% to 60%. This pulse travels through the flow cell and generates a number of echoes, which form the echo train shown in FIG. 4. Using software, the digitized signal provided by converter 86 is gated to select the appropriate echoes, then a Fourier transform (implemented as the FFT algorithm) is used to convert the time domain signal into the equivalent frequency domain signal (i.e., the spectrum) for each distinct echo.

Figure 4:
FIG. 4 is a graph showing the echo train received for a single input pulse.

The first echo in FIG. 4 travels across twice the diameter of the flow cell of FIG. 2, the second echo travels four times the diameter, and subsequent echoes travel correspondingly farther distances. An analysis of the returning echoes reveals that they are attenuated by the following amounts:

attenuation of first echo=$2I+R+2A$ attenuation of second echo=$2I+3R=4A$ where I=insertion loss (dB), R=reflection coefficient (dB), and A is the total absorption (dB) in the suspension for a path length equal to one diameter of the flow cell. Each of the foregoing terms is a function of frequency. Therefore, subtracting the spectrum of the second echo from that of the first yields a difference signal Difference=$2(R+A)$.

It is expected that the term R will be small compared to the quantity of interest A, and that furthermore, the term R will tend to change slowly with time. Therefore, the difference signal represents the total absorption plus a small offset. Dividing this difference spectrum by the distance 2d, where "d" is the diameter of the flow cell, yields the frequency dependent attenuation coefficient $\alpha(f)$. Thus a single echo train provides information about the spectral content of ultrasonic pulses corresponding to a number of acoustical path lengths, without moving the transducer. This technique allows one to look for any degradation of the sensor by comparing the signals from two different acoustic paths.

This "Multiple-Echo Spectroscopy" technique is accomplished by detecting a first echo of the first pulse that has traveled over a first path length and determining the spectrum of the first echo; detecting a second echo of the first pulse that has traveled over a second path length and determining the spectrum of the second echo; determining the difference between the first echo spectrum and second echo spectrum and dividing the difference by the difference between the first path length and second path length to obtain an attenuation independent of system variations.

Also, the system of a reflector and a combination transmitter and receiver, as in FIG. 2, compared to no reflector and a separate transmitter and receiver (one of which would have to move to collect degradation information), as in FIG. 1, is a lower cost system for collecting the required ultrasonic spectra.

Figure 5A:
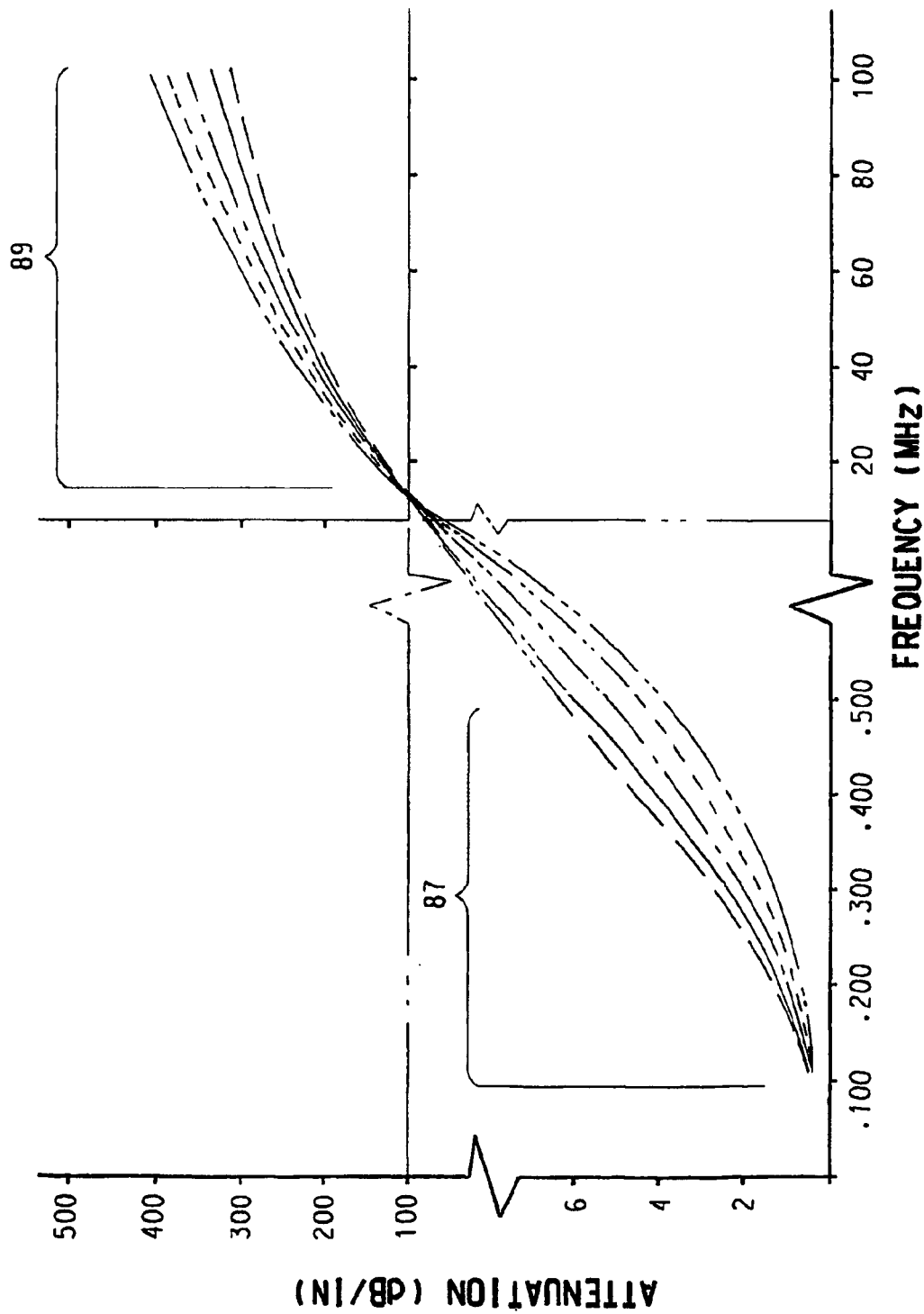
FIG. 5A shows a general variation of attenuation and frequency over broad ranges.

The technique just described depends upon the total attenuation being sufficiently low to allow an ultrasonic pulse to propagate across a distance equal to several diameters of the flow cell. The prior art strongly favors the choice of high frequencies (above about 50 MHz), where the attenuation is very strong for high concentration suspensions, or slurries, of sub-micron particles. FIG. 5A shows a qualitative description of attenuation coefficient (dB/in), or just attenuation, for several particle sizes (0.20–0.28 m) over a wide range of frequencies where the low frequency regime 87 is shown in an expanded scale compared to the high frequency regime 89.

Figure 5B:
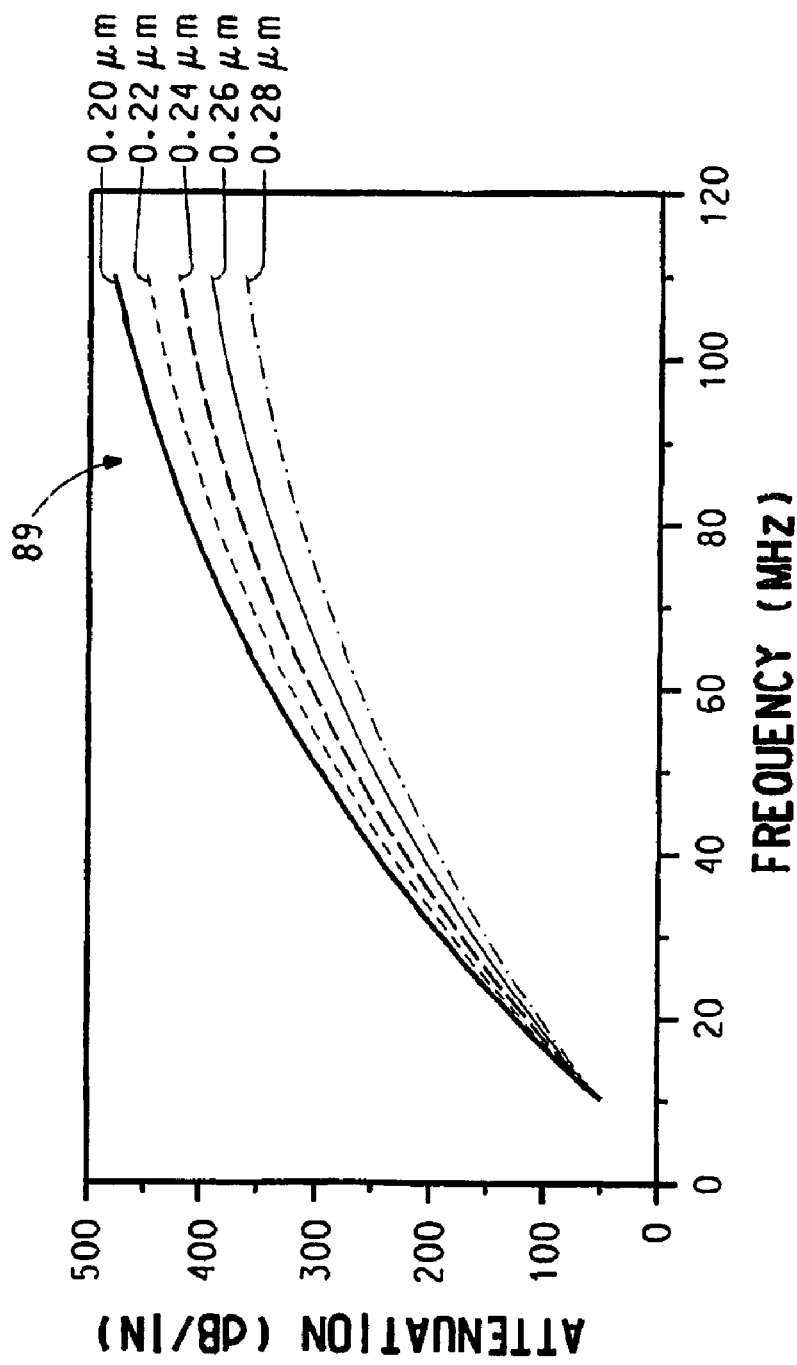
FIG. 5B is a graph showing the calculated attenuation from 10–100 MHz for 2% vol. concentration of a sample of sub-micron particles in water.

FIG. 5B shows the attenuation for several particle sizes (0.20–0.28 $\mu$m) in the high frequency regime 89 at a concentration of about 2% as calculated with the Allegra-Hawley model, which has been confirmed by empirical results. It is evident that even at low concentrations (2% concentration as shown in FIG. 5B), the attenuation loss is so high (250–450 dB/in) that the gap 26 between transducers shown in FIG. 1 can be at most a small fraction of an inch (less than 2.54 cm) for practical ultrasonic energy levels. Such a gap would be inappropriate for on-line applications where the suspension would quickly clog the gap. In addition, multiple echoes could not be distinguished in a system with such a small gap. It should be noted in FIG. 5B that the differentiation between different particle sizes becomes more distinct as the frequency is increased. Thus, the natural inclination, as evidenced by the prior art, is to move towards higher frequencies. This choice of frequency regime is incompatible with the present invention having a large gap, of preferably at least about 0.25 inches (0.64 cm), when there is a high concentration of particles, and especially sub-micron particles.

Figure 5C:
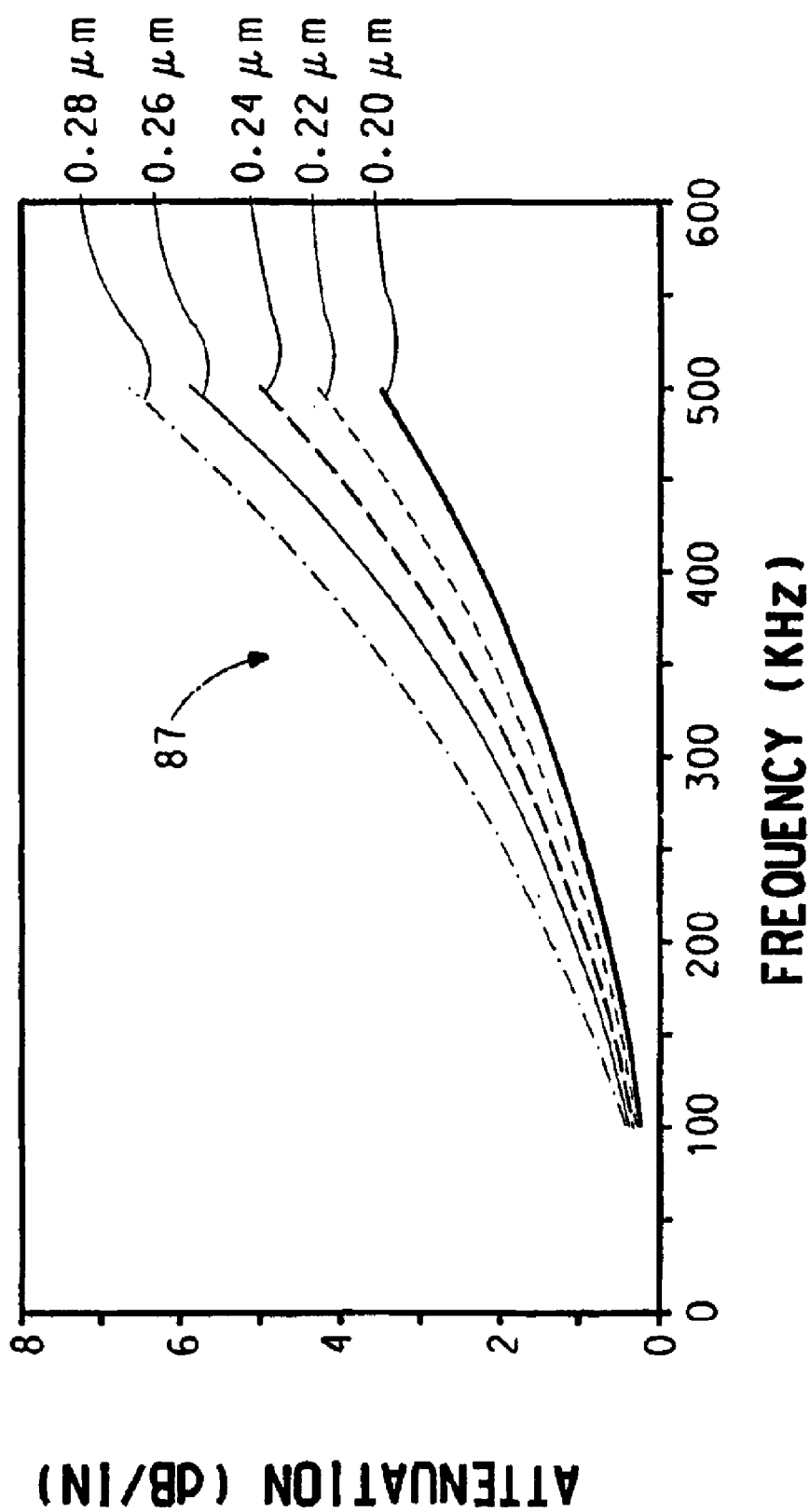
FIG. 5C is a graph showing the calculated attenuation from 100–500 kHz for 20% vol concentration of the same sample as in FIG. 5B.

In the case of a high concentration of particles, particularly sub-micron particles, a better choice of a frequency range is below 50 MHz and preferably below 1 MHz. FIG. 5C shows the attenuation (dB/in) calculated in a 100–500 kHz range at a concentration of about 20%. In spite of the higher concentration (20% shown in FIG. 5C), the attenuation is two orders of magnitude smaller. Thus the propagation distance can be long enough to allow Multiple Echo Spectroscopy to be used. At 500 kHz, the attenuation curves in FIG. 5C show as much relative differentiation as they do at 100 MHz in FIG. 5B. Therefore no loss of sensitivity using a large gap (of at least 0.25 inches, 0.64 cm) is expected in this frequency regime.

The prior art teaches that by determining the absorption coefficient $\alpha_{ij}$ at many frequencies $f_j$ (using the Allegra-Hawley model for example) and the absorption spectrum $A_j$ of an unknown suspension, it is possible to determine the PSD in terms of the concentration of particles $c_i$ at each size i simply by solving (i.e., inverting) the linear equation below:

$$A_j = \sum_{i=1}^{n} \alpha_{ij} c_i$$

Figure 6:
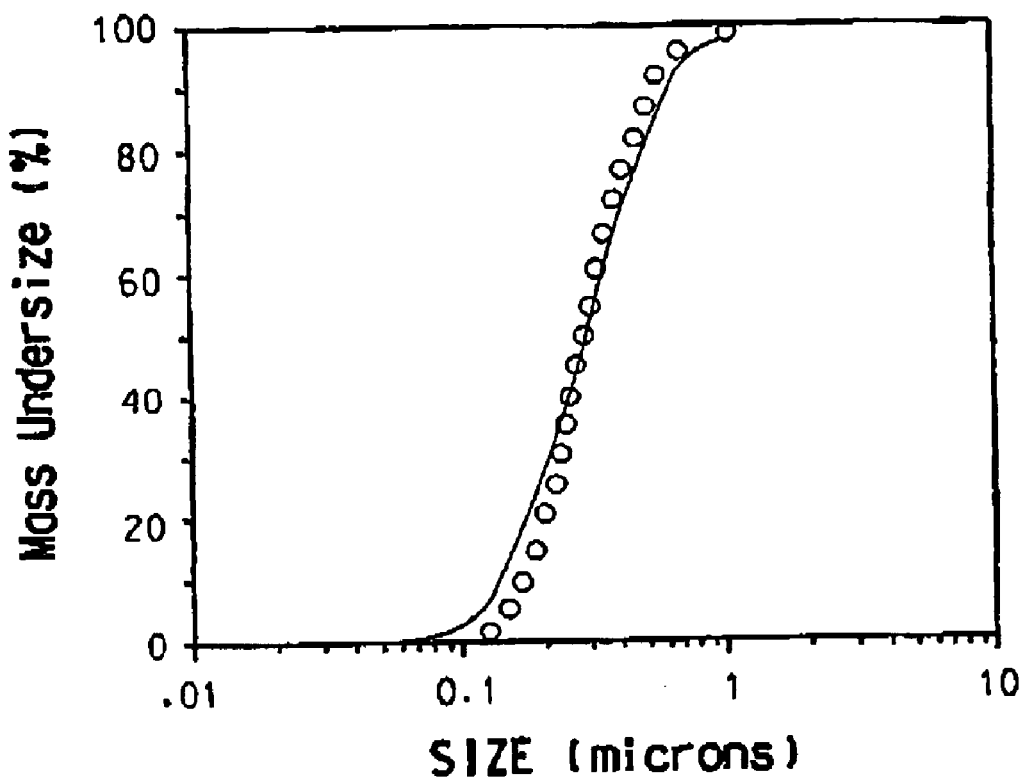
FIG. 6 is a graph showing a comparison between the PSD measured with this invention and the PSD measured via conventional means.

Past experience shows there is so little information in the attenuation spectra for sub-micron particles that inversion of the linear equation is very unstable and yields only 2 or 3 non-zero size classes. It has been found that the only robust method of extracting particle size information out of measured spectra is to parameterize the PSD. A simple example is the assumption of a log-normal distribution for the PSD function. By integrating the Allegra-Hawley attenuation over a log-normal distribution, the number of free parameters is reduced to three: concentration, mean size, and distribution width. These quantities can be extracted by fitting the parameterized model to the ultrasonic spectrum. An example of the results of this approach is depicted in FIG. 6. For a given sample, the results from the monitor of the invention are indicated by the solid line 97 showing the cumulative size distribution of the particles. The data curve depicted with circles, such as circle 99, indicate the results of the same sample analyzed with a conventional Brookhaven x-ray disc centrifuge. The results obtained with the monitor compare favorably with the results of the Brookhaven instrument.

The reflector must be designed to suppress reverberations that cause extraneous echoes to be received by the transducer. A simple metal plate (or the opposite wall of the pipe) will generally give a confusing echo train that is difficult to interpret. For example, the power reflection coefficient at a water/steel interface is about 88%. Therefore about 12% of the ultrasonic energy enters the steel; at the far wall of the reflector most (88%) of this energy is reflected. After a reverberation time equal to twice the reflector thickness divided by the speed of sound in steel, about 12% of this internal energy emerges as a back surface reflection. The acoustic energy trapped in the reflector continues to be emitted at constant intervals (equal to the reverberation time) until the energy is dissipated. Depending on the material and geometry of the reflector and the transducer-reflector spacing, these back surface echoes will arrive at the transducer at about the same time as the desired front surface reflection; the spurious signal will have an intensity about 18 dB below that of the desired signal, which is sufficiently strong to distort the ultrasonic wave. The Fourier transform of the distorted wave will yield a spectrum that does not accurately capture the frequency dependent attenuation of the suspension itself as has been observed.

Figure 7:
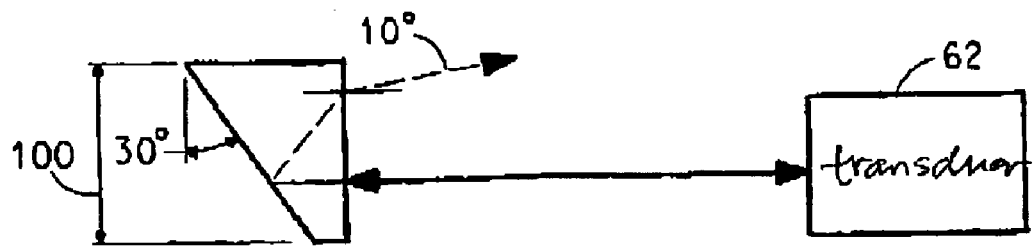
FIG. 7 is a side view of a reflector for ultrasonic energy.

There are many methods to reduce the reverberations produced by the reflector. One might be to place impedance matching layers or an acoustic absorber on the back surface. An alternative approach is shown in FIG. 7, but it should be understood that this example is not the only solution to the problem of reverberation. FIG. 7 shows a side view of a reflector made from 316 stainless steel round bar stock. The diameter 100 is approximately 1.5 inches (3.81 cm); one end has been milled away at a 30° angle, and both ends have been sanded to a smooth finish. The ultrasonic beam is incident at right angles to the reflector on the right side of the figure; 88% of the sound is reflected and 12% enters the reflector. Upon reaching the back surface of the reflector, the internal sound beam is reflected at an angle due to the inclination of the surface. When this secondary beam reaches the front surface, it is incident on the front interface at a 60° angle. Due to Snell's Law, this sound beam is refracted and emerges into the suspension at about 10° from the normal. The central part of this delayed and refracted beam misses the transducer, which is about 2 inches (5.1 cm) from the reflector. Also, the main lobe of the transducer's sensitivity pattern (assuming 500 kHz and a transducer diameter of 1 inch (2.54 cm)) only extends to 8.4°; therefore, the only echoes seen by the transducer are those due to front surface reflections.

Figure 8:
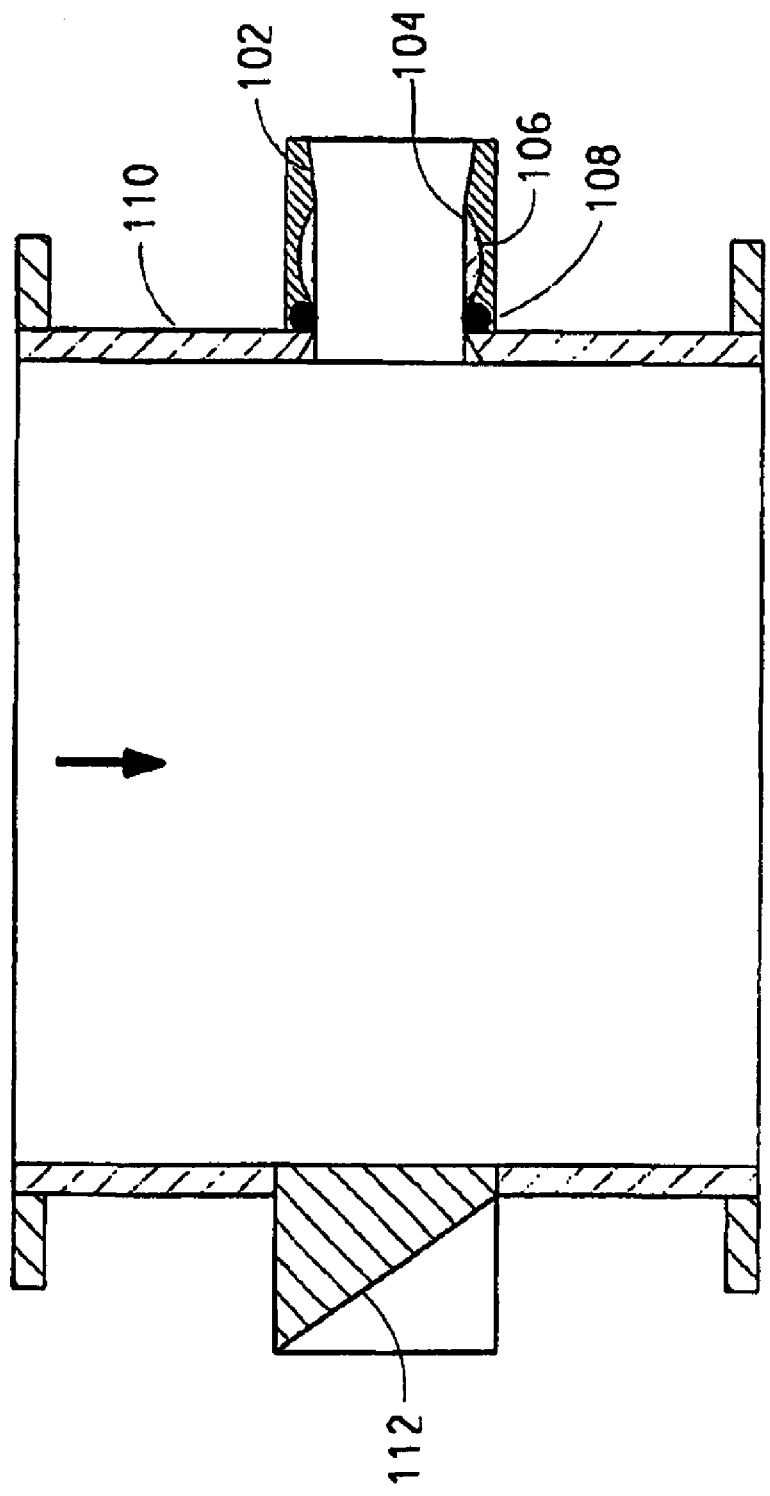
FIG. 8 is a section view of a spool piece for a particle suspension process line with a mounting for an ultrasonic transducer and reflector.

Without proper alignment of the transducer with respect to the reflector, phase cancellation effects will distort the received signal at high frequencies (above 20 MHz). The transducer 102 shown in FIG. 8 is mounted in a bore 104 in a spherical bearing 106 (which provides both gimbal and swivel). The transducer acts as a transmitter for the pulse of ultrasonic energy and thereafter acts a receiver for the reflected signal. The bearing 106 is sealed to the flow cell with an o-ring 108. This o-ring provides some measure of acoustic and electrical isolation between the transducer and the rest of the system. Since mechanical sources of acoustical noise tend to be in the low frequency range, the main concern here is with shear waves (produced by mode conversion) coupling into the transducer. The transducer 102 and its mounting are part of a spool piece 110 that would bolt into an existing pipeline and would become an integral part of the equipment. A reflector 112, as discussed referring to FIG. 7, would be placed in the spool piece opposite the transducer.

Figure 9:
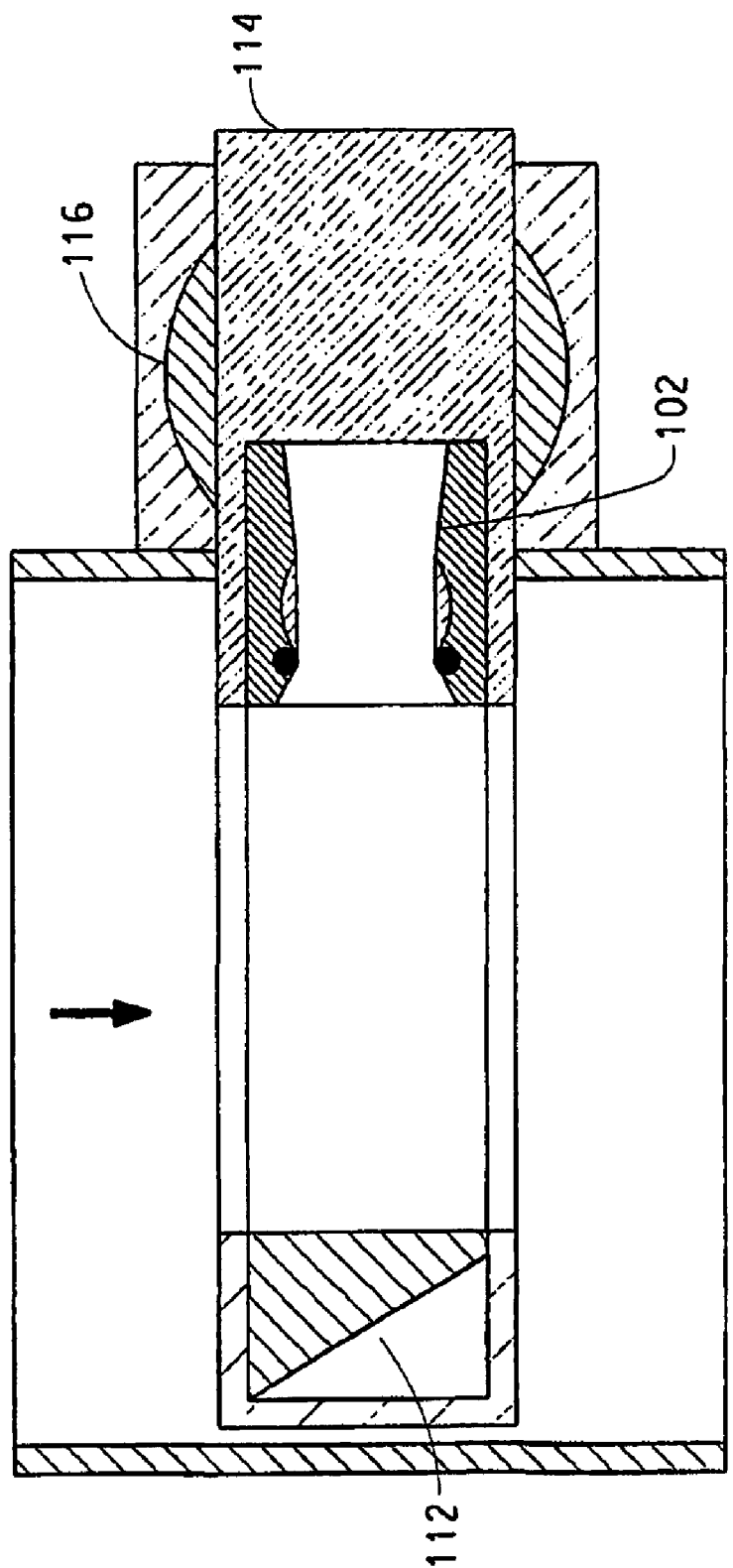
FIG. 9 is a section view of a probe-type assembly of a transducer and reflector in a spool piece for a particle suspension process line.

An alternative to the arrangement of FIG. 8 is an insertable probe 114 shown in FIG. 9. The probe would contain both transducer 102 and reflector 112, and it could be inserted through the bore of a ball-valve 116 into an existing process stream. The attraction of the probe is that is can be inserted or removed while the process is running. The transducer acts as both a transmitter and receiver as in the embodiment of FIG. 8.

Figure 10:
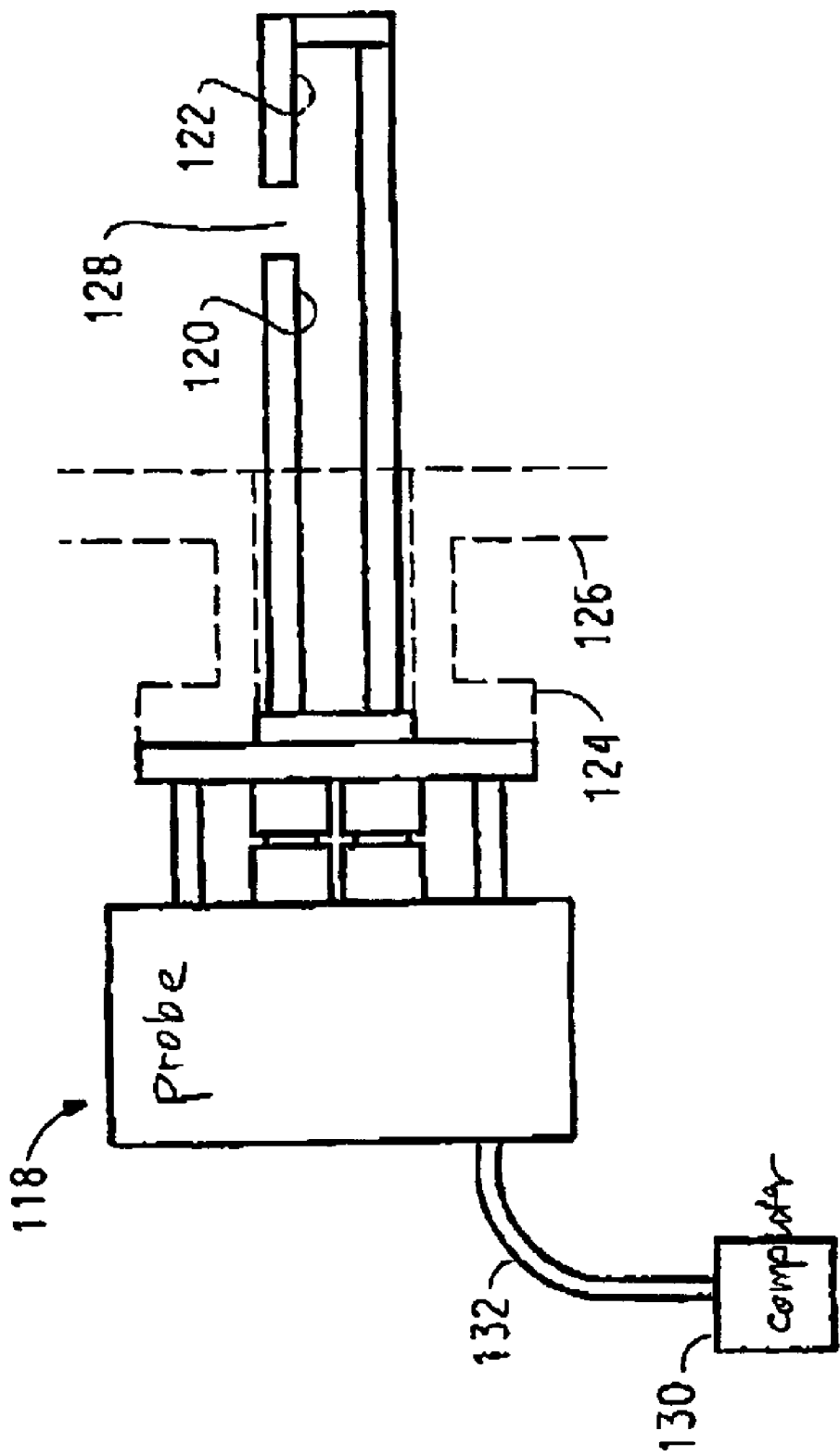
FIG. 10 is a side view of an insertable probe that contains both a transducer transmitter and a transducer receiver attached to a flange fitting on a particle suspension process line or vessel.

A further alternative arrangement is shown in FIG. 10 in which an insertable probe 118 contains both an ultrasonic transducer transmitter 120 and an ultrasonic transducer receiver 122. The probe is attached to a flange fitting 124 in a process vessel or pipe 126 shown in dashed lines. The transmitter 120 and receiver 122 are separated by a gap or sensing volume 128 that is large enough not to become clogged with the suspension being analyzed. The received ultrasonic signal is amplified and conveyed via a 200 MHz bandwidth fiber optic link 132 to the attenuator and digitizer residing in the computer 130. This is also the preferred way to connect a computer for the arrangements of FIGS. 8 and 9.

Figures 1, 11:
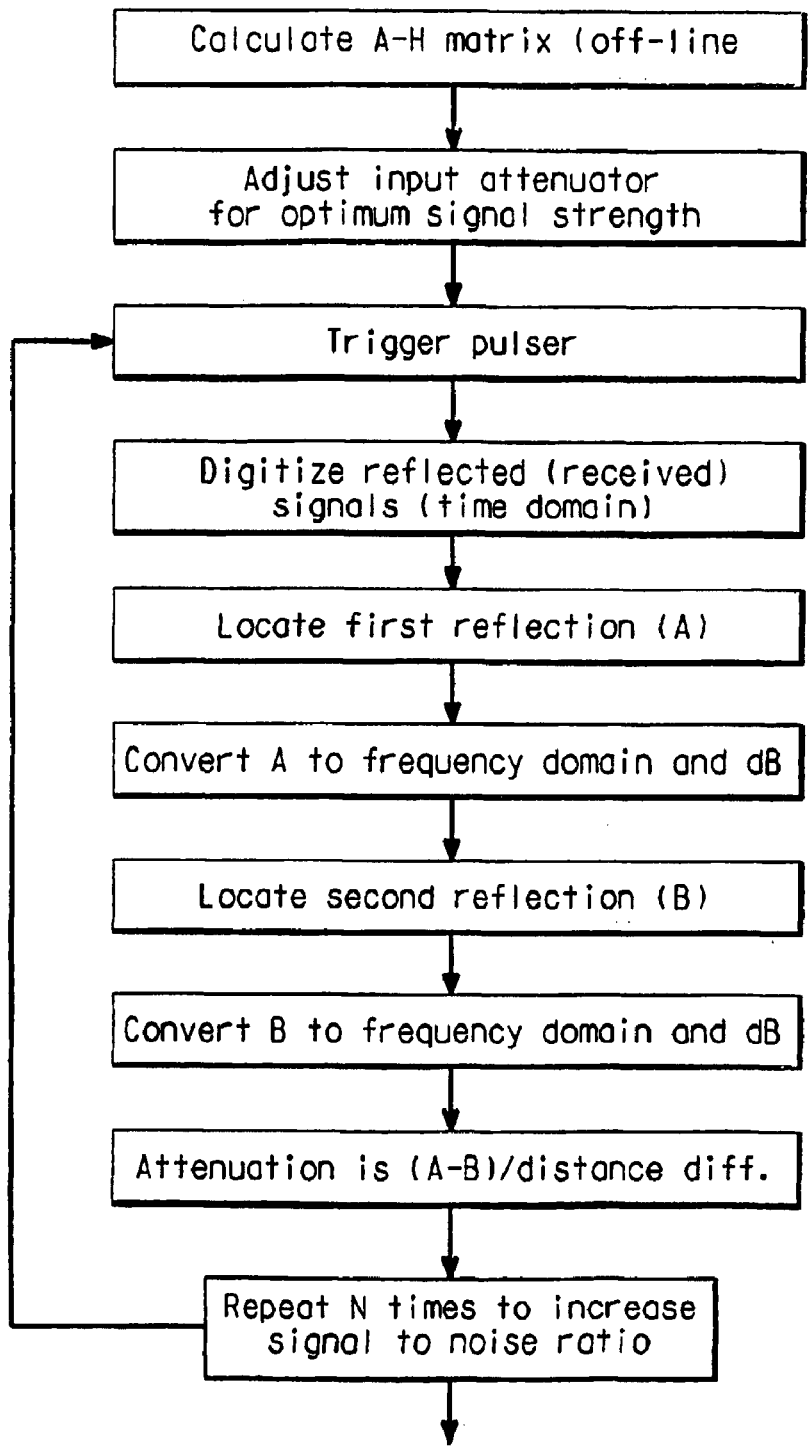
FIG. 11 is a block diagram of a typical control system for the particle size analyzer.
Figures 2, 11:
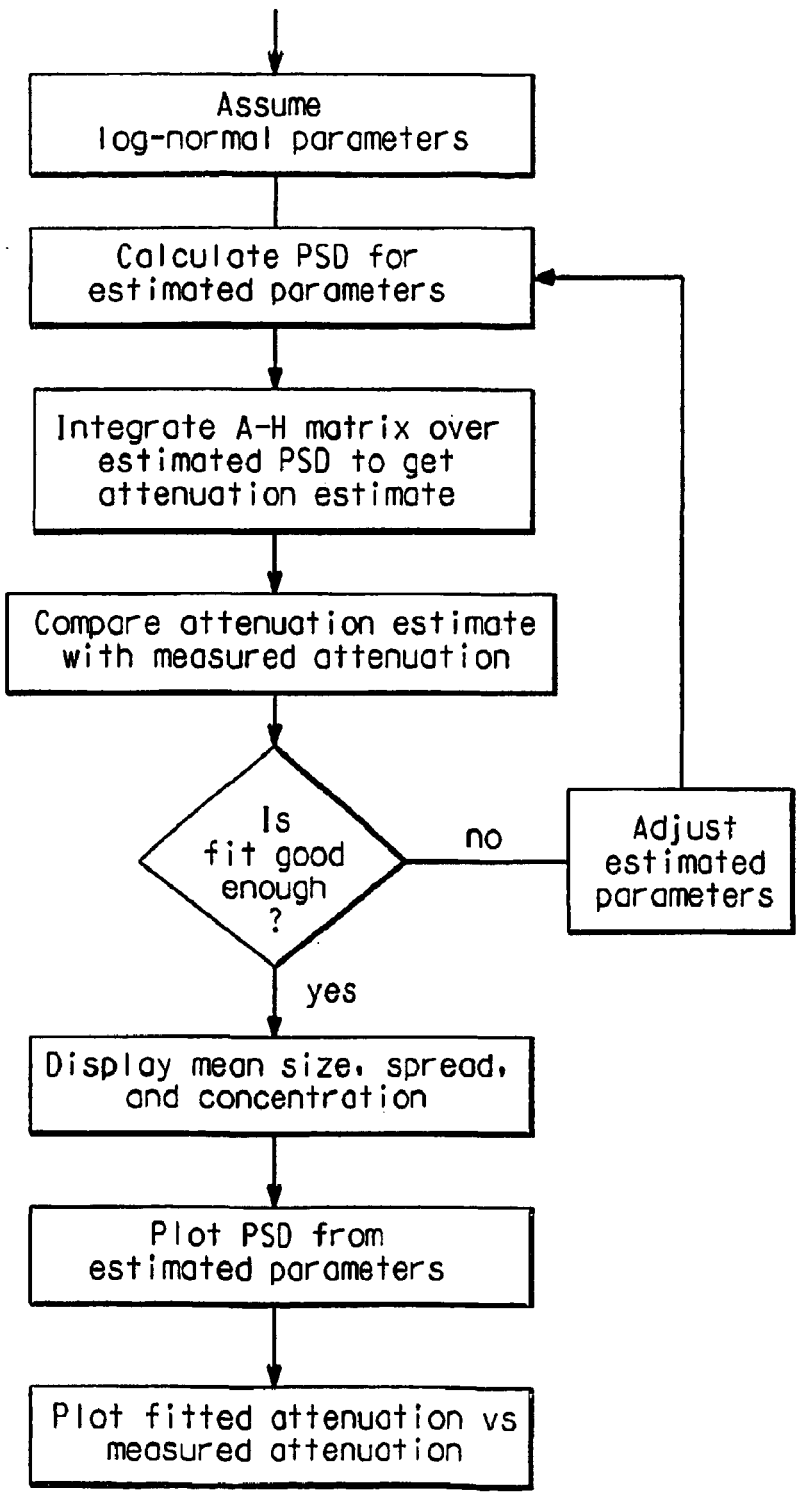

In order to convert the measurements of frequency-dependent attenuation into particle size distribution (PSD), a physical model is needed to give the relation between attenuation and particle size. It is useful to employ the Allegra-Hawley model because it is valid for both dispersions and emulsions. This model is used to calculate the expected attenuation as a function of particle diameter and frequency. The resulting matrix of pre-calculated values is stored in the computer. When measurement is made, a fitting routine is used,to determine the best estimates of the log-normal parameters (median size, spread, and concentration) that define a PSD over which the Allegra-Hawley matrix is integrated, so that the resulting predicted attenuation agrees with the observed attenuation. A simplified flow chart is shown in FIG. 11 is one example of a way of operating the system of FIG. 2. It involves use of the Allegra-Hawley model and as such is limited to dilute aqueous suspensions of less than about 15% by volume solids concentration and less than about 50% by volume liquid in liquid concentration for emulsions. For higher concentrations one solution is to handle the suspension with an automated sampling system that dilutes the suspension to appropriate levels to use Allegra-Hawley. The Allegra-Hawley matrix is first calculated off-line for a range of particle size distributions and the results are stored for later use on the computer 90. The ultrasonic transducer 62 is triggered by the pulser 82 and the reflected signals are collected, preamplified with amplifier 84 having the logarithmic stage 85, and digitized with a high speed A/D converter 86. The digitized signals are analyzed to locate the first reflection (A) and second reflection (B) which are converted to transmission spectra (dB vs. frequency). The attenuation is determined by the formula attenuation=(A−B)/distance, where the distance is the path length of the signal from transmitter to receiver, which in the case of the reflector system in FIG. 2, would be the distance from the transducer face (acting as a transmitter) to the reflector face and back to the transducer face (acting as a receiver). This treatment eliminates the effect of undesired transducer output drift. To increase the signal to noise ratio, this cycle would be repeated about 50 times and the 50 attenuation spectra averaged. The measured average signal would be compared to the expected attenuation (based on an estimate of the PSD and the stored Allegra-Hawley matrix) to determine if there is a good fit. If the fit is not good enough, an adjustment is made to the estimated PSD and the attenuation is compared again until a good fit is obtained. The particle size distribution determined is displayed as an output showing median size, spread, and concentration. The measured attenuation is plotted against the best fit estimated attenuation.

The flow chart of FIG. 11 can be modified to accommodate the transmitter/receiver arrangement of FIG. 10 or something similar to the prior art arrangement of FIG. 1 (through transmission systems) by eliminating the steps for looking for reflections. Transducer drift could be corrected for by some other means, such as moving one transducer and comparing the signals from the two different path lengths. For transducers where stability and rapid buildup of particles on the transducer is not a concern, routine corrections for drift may not be necessary. The flow chart can also be modified to apply to slurries with particle concentrations greater than 20% by substituting an empirical model for the Allegra-Hawley calculation. Such empirical estimating steps are found in the '629 reference to Alba. The system of the invention is especially useful where the particle distribution includes sub-micron particles and the suspension has more than 20% by volume of particles. In this case, a low frequency ultrasonic wideband signal would be employed.

One application of the particle size measuring system is in a milling process where a material, such as $CaCO_3$ is being broken down into fine particles for an intended use. In the case of the milling monitor, referring to FIGS. 2 and 11, the steps involve:

making a flow cell with a two inch (5.1 cm) inner diameter and a wideband transducer mounted opposite an ultrasonic reflector so that the physical gap between them is two inches (5.1 cm) (giving an acoustical path length of four inches, 10.2 cm);

generating a wide bandwidth ultrasonic pulse at a center frequency of about 500 kHz and a frequency range spanning 200 kHz to 800 kHz and injecting it into the suspension;

receiving an attenuated wide bandwidth ultrasonic pulse at a center frequency of about 500 kHz and a frequency range spanning 200 kHz to 800 kHz that has passed through the suspension;

preamplifying the received attenuated signal with a logarithmic amplifier stage;

digitizing the preamplified signal with a digitizer with a 10 MHz sampling rate;

gating the digitized signal to eliminate "ringing" developed within the transducer faceplate;

applying a Fourier transformation (e.g. FFT) to the signal;

subtracting the baseline signal for water to get a preprocessed signal;

dividing the preprocessed signal by the acoustical path-length to determine a normalized attenuation (dB/in);

assuming a log normal size distribution;
calculating an assumed PSD using estimated log-normal parameters (median size, distribution width, concentration);
using the Allegra-Hawley model (or other theoretical or empirical model) to calculate the expected ultrasonic attenuation based on the calculated PSD;
comparing the fit of the expected ultrasonic attenuation to the observed normalized attenuation. Iterate by adjusting the estimate of the log-normal parameters until a best fit is obtained;
estimating the PSD based on the final estimate of the log-normal parameters.

A similar application involved milling of $TiO_2$ using two transducers (through transmission mode) mounted in a two inch (5.1 cm) diameter flow cell (giving a two inch (5.1 cm) gap). It is contemplated that in the absence of a reliable theoretical model (such as may be the case at very high concentrations), this method may be adapted to estimate the relative change in PSD by comparing the normalized attenuation signal to empirical attenuation data corresponding to a variety of particle size distributions for that process material. It is further contemplated that this method can be applied to other PSD models besides the log-normal model.

Figure 12:
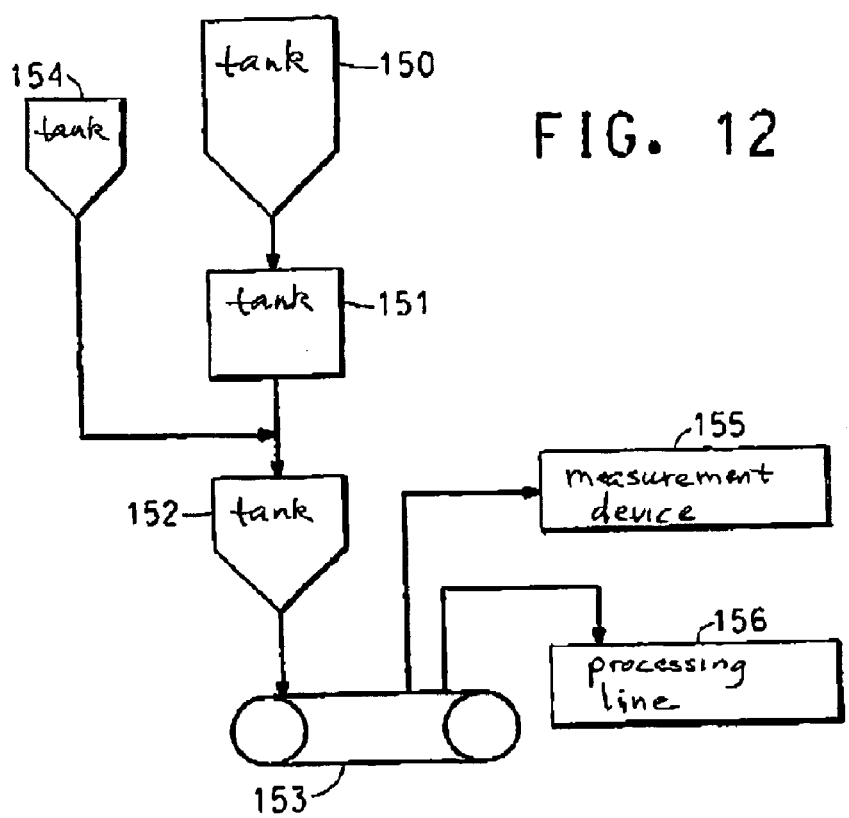
FIG. 12 is a diagram of a silver precipitation process.

Another application of the particle size measuring system is for a dilute suspension, or dispersion, where the particle size is changing and where the particles are sub-micron and are 15% or less by volume. In this case, a high frequency wideband ultrasonic signal would be employed. One such application is described in FIG. 12 showing a silver precipitation system. The system comprises a master batch solution tank 150, a sub-batch weigh tank 151, a second solution tank 154, a sub-batch precipitation tank 152, a filter and wash device 153, an off-line size measurement device 155, and a particle-to-paste processing line 156. A master batch of silver solution is prepared from a metal salt solution, such as silver nitrate, to which is added MEA (monoethanolamine) to form a solution A at 150 in which aging and growth of particles occurs. It is desired to remove solution A in sub-batches to precipitate out the silver when the aging process has reached at point at which particles of the desired size can be produced. The sub-batch is weighed out and collected in tank 152 and a given quantity of reducing agent, solution B at 154, is added to precipitate silver particles which are then filtered, washed, and freeze dried to be used later in the process to provide a desired end product, such as a paste. Additional details of this process can be found in the '122 reference to Glicksman, incorporated herein by reference. In the past, it was not accurately known when to withdraw the sub-batch to achieve the desired silver particle size. In the past, it was thought that a period of aging of about 16 hours was required. It was also not known how the master batch particle size continued to vary over the time multiple sub-batches were withdrawn. The master batch aging particles are changing in size early in the process and any sample pulled would still be so reactive that accurate particle size could not be obtained from a withdrawn sample. By applying the particle size sensing system of the invention at the master batch tank 150, a relationship was discovered between the attenuation signal of the aging particles and the final silver particle size.

Figure 13:
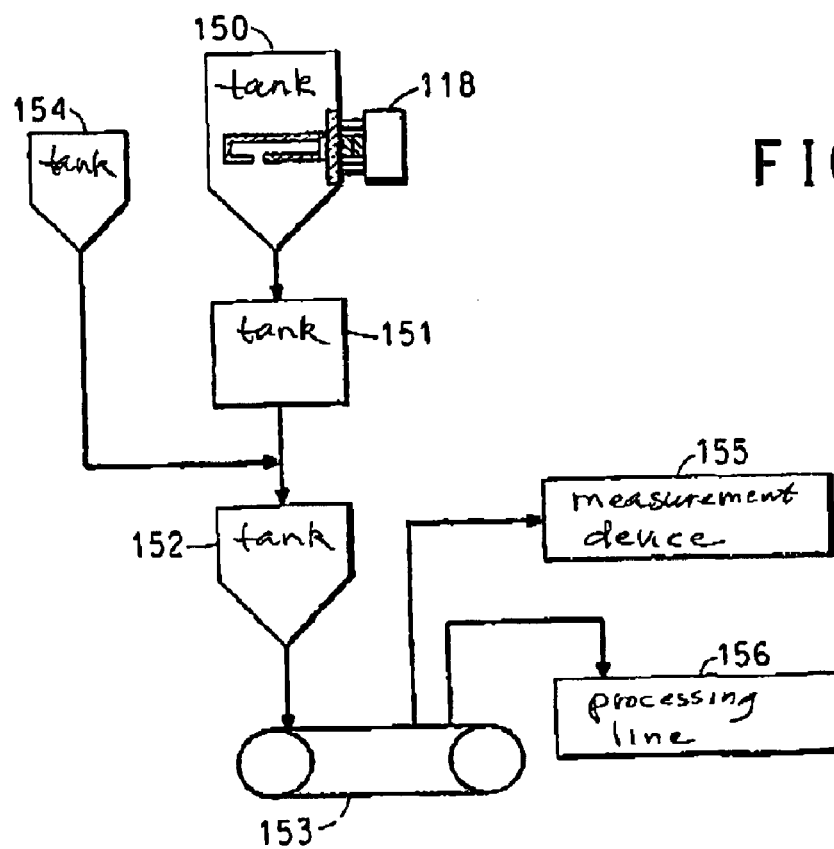
FIG. 13 is a diagram of a particle size analyzer applied to the process of FIG. 12.

FIG. 13 shows the probe 118 of FIG. 10 located near the bottom of stirred tank 150. An experiment was run to study changes in the ultrasonic attenuation due to aging of solution A in tank 150 and relate that to desired silver particle size obtained from tank 152. The attenuation was measured continuously starting with the addition of MEA to the silver nitrate solution. A background reading was taken using deionized water. The probe was operated at 50 MHz with a transducer gap 128 (FIG. 10) of about ¾ inch (1.9 cm). The probe is also known to work at 30 MHz with a transducer gap of about 1¾ inches (4.4 cm). Periodically, a sample was drawn from tank 150 and combined with a fixed concentration of solution B to produce silver particles by precipitation. These silver particles were later imaged via SEM and the resulting images were analyzed to determine silver particle size. The images were analyzed using NIH Image software to determine the average and standard deviation of the particle diameter for 20 particles.

Figure 14:
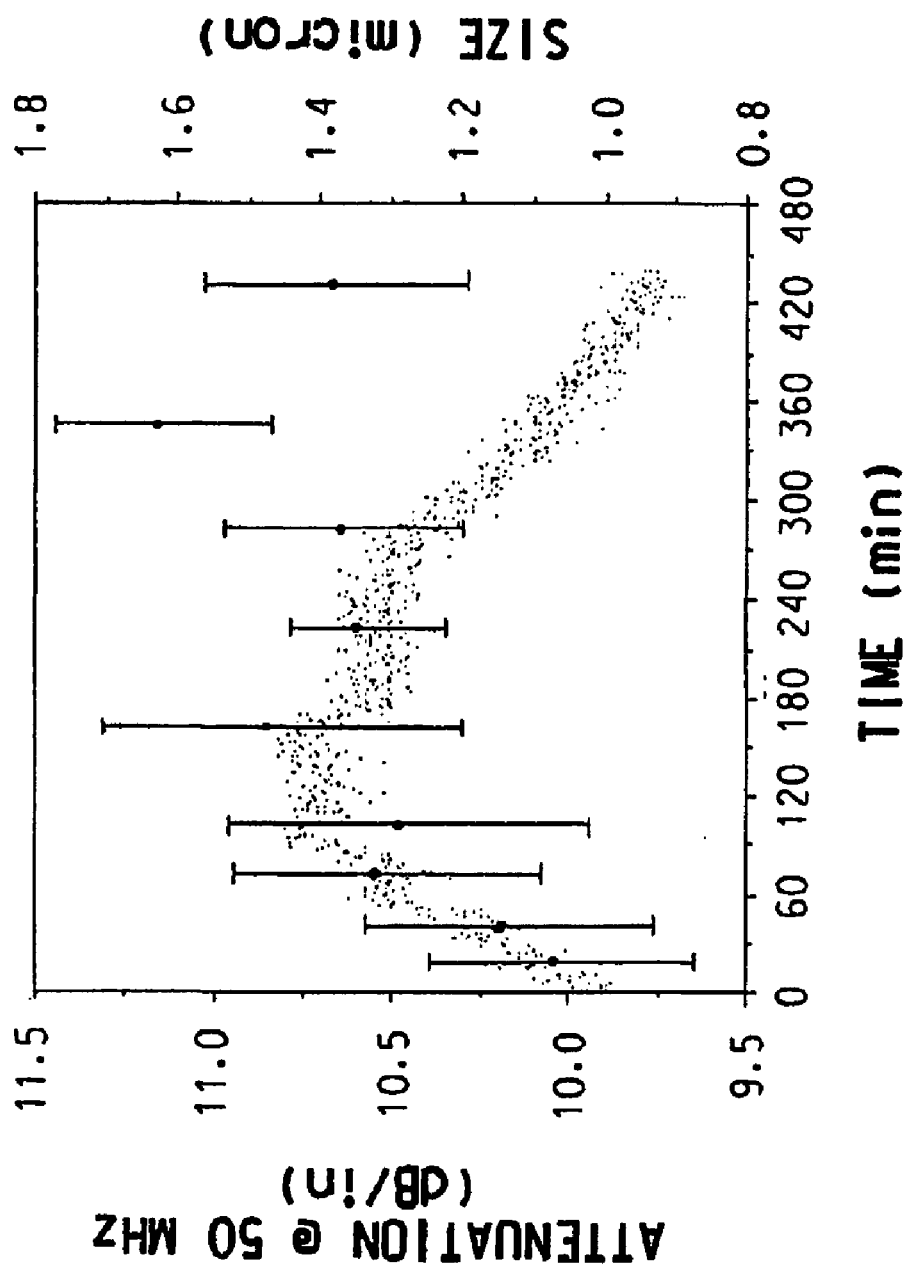
FIG. 14 is a plot of attenuation in an aging silver solution (versus time) and the size of the corresponding precipitated silver particles in the process of FIG. 13.

The attenuation and size data are compared in FIG. 14. It is evident that the attenuation of the aging particles in solution A (shown as small dots) rises and corresponds with an increasing particle size of the precipitated silver particles (shown as a filled circle representing the average particle size and a line representing the particle size range of the 20 particles in the sample). The attenuation scale is on the left and the particle size scale is on the right of the plot. The aging time (i.e., when the sample was drawn and precipitated) is shown on the horizontal axis. The attenuation and particle size increase with aging time until a plateau is reached in particle size and the attenuation decreases at about 180 minutes of aging.

The test indicates the particle size analysis system is capable of monitoring the aging process in solution A, and there is a predictable relationship between the attenuation and the final silver particle size. It is known that the particle size can be adjusted by varying the composition of solution B. In the past this adjustment could only be done by trial and error since the particle size was not known until one sub-batch was treated with solution B and the particle size measured by device 155. Then adjustment could be made on the next sub-batch. This adjustment may be off, though, since the aging process changes the particle size from one sub-batch to the next. Sometimes sub-batches would have to be blended to compensate for undesirable particle size variation, adding cost and time to the production process. By knowing the variation in aging particle size using the monitor, the composition of solution B can be determined with greater certainty so the particle size of the silver particles can be maintained relatively constant regardless of when the sub-batch is withdrawn from the master batch.

Figure 15:
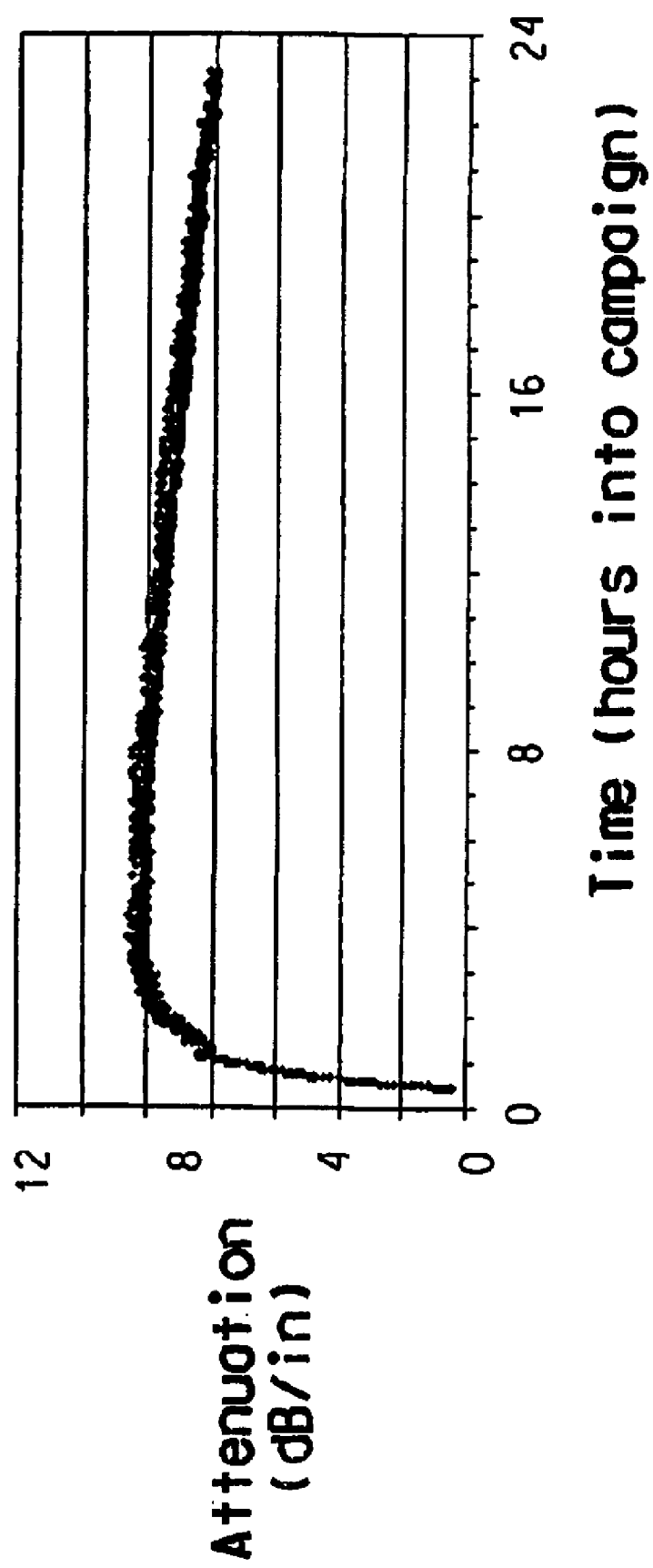
FIG. 15 is a plot of long term attenuation data illustrating the aging process in the production of silver particles.

These measurements of solution A can be made in-line in real-time at a silver particle plant. FIG. 15 illustrates that the initial aging process has completed after only about 3 hours, so a campaign of multiple sub-batches can be started after 3 hours instead of after the 16 hours that was previously considered necessary. This discovery provides a basis for a shortened aging cycle that could increase productivity at the plant by 20%. As the master batch ages and the attenuation slowly decreases as seen in FIG. 15, the PSD monitor can be used to regulate the concentration of solution B to add to a particular sub-batch to get a predictable, uniform, silver particle size from the different sub-batches. Each master batch may also be slightly different from other master batches so compensation can be made from master batch to master batch by monitoring the aging particle size. It is believed the invention can be usefully applied to other precipitation processes for precipitating particles from a solution, such as processes for precipitating a metal particle from a metal salt solution to obtain particles of gold, palladium, platinum and the like.

What is claimed is:

1. A particle size distribution monitor, comprising:
 (a) a transducer adapted to be a source of ultrasonic energy and positioned in contact with a suspension containing a percent by volume of particles in a liquid, the transducer transmitting ultrasonic energy through the suspension wherein the energy comprises a wideband pulse containing a range of frequency components;

(b) a transducer adapted to be receive of ultrasonic energy and positioned in contact with said suspension to receive said wideband range of ultrasonic energy which has passed through the suspension;

(c) first means adapted to accept a signal from said receiver and make an instantaneous determination of the attenuation of the wideband ultrasonic energy in passing through the suspension comprising (i) an A/D digitizer for said signal, (ii) an FFT analyzer for the digitized signal, (iii) means to obtain the magnitude of the FFT data representing the measured attenuation, and (iv) means of controlling an additional attenuation of said signal from the receiver before it is processed by the A/D digitizer; and (d) second means comprising means to determine an estimated PSD and means to compare the estimated PSD with the measured attenuation and determine the goodness of the fit.

2. A particle size distribution monitor, comprising:

(a) a transducer adapted to be a source of ultrasonic energy and positioned in contact with a suspension containing a percent by volume of particles in a liquid, the transducer transmitting ultrasonic energy through the suspension wherein the energy comprises a wideband pulse containing a range of frequency components;

(b) a transducer adapted to be a receiver of ultrasonic energy and positioned in contact with said suspension to receive said wideband range of ultrasonic energy which has passed through the suspension;

(c) first means adapted to accept a signal from said receiver and make an instantaneous determination of the attenuation of the wideband ultrasonic energy in passing through the suspension that is a computer that is remotely positioned from the transducers and is connected to the transducers by a fiber optic cable.

3. A method of monitoring the particle size distribution of particles in a suspension under dynamic conditions, comprising the steps of:

transmitting a first pulse of ultrasonic energy containing a wideband range of frequency components through the suspension which attenuates the pulse;

receiving the attenuated pulse after it has passed through the suspension;

developing a first signal representative of the attenuated first pulse;

digitizing the first signal with a high speed analog-to-digital converter to form a time domain signal;

applying a Fourier.trensform to convert the time domain signal to an equivalent frequency domain signal, or spectrum, for each signal;

converting the spectrum into dB to express the attenuation as a function of frequency;

reflecting the first pulse with a reflector;

detecting a first echo of the first pulse that has traveled over a first path length and determining the spectrum of the first echo;

detecting a second echo of the first pulse that has traveled over a second path length and determining the spectrum of the second echo;

determining the difference between the first echo spectrum and second echo spectrum and dividing said difference by the difference between the first path length and second path length to obtain an attenuation corrected for system variations.

4. A method of utilizing particle size monitoring to control a process for precipitating particles, comprising:

to collect data continuously about the attenuation of an ultrasonic pulse passed through a master batch of a solution which has a particle size that is changing;

generating a signal when the particle size reaches a predetermined attenuation value;

withdrawing a sub-batch of solution after the signal is generated;

predetermining a concentration of a second solution to be added to the withdrawn sub-batch based on the measured attenuation signal at the time of withdrawal;

adding said predetermined concentration of second solution to the sub-batch to precipitate particles.

5. The method of claim 4, wherein the master batch is a metal salt solution and the particles precipitated are metal particles.

6. The method of claim 5, wherein the metal salt solution is a silver salt solution and the particles precipitated are silver particles.

* * * * *